(12) United States Patent
Pellicciari

(10) Patent No.: US 9,243,027 B2
(45) Date of Patent: *Jan. 26, 2016

(54) TGR5 MODULATORS AND METHODS OF USE THEREOF

(71) Applicant: Intercept Pharmaceuticals, Inc., New York, NY (US)

(72) Inventor: Roberto Pellicciari, Perugia (IT)

(73) Assignee: INTERCEPT PHARMACEUTICALS, INC., New York, NY (US)

(*) Notice: Subject to any disclaimer, the term of this patent is extended or adjusted under 35 U.S.C. 154(b) by 218 days.

This patent is subject to a terminal disclaimer.

(21) Appl. No.: 13/854,579

(22) Filed: Apr. 1, 2013

(65) Prior Publication Data

US 2014/0094443 A1    Apr. 3, 2014

Related U.S. Application Data

(63) Continuation of application No. 12/523,670, filed as application No. PCT/US2008/000658 on Jan. 18, 2008, now Pat. No. 8,410,083.

(30) Foreign Application Priority Data

Jan. 19, 2007 (EP) .................................... 07001143
Jun. 20, 2007 (EP) .................................... 07012079

(51) Int. Cl.
| | | |
|---|---|---|
| *A61K 31/575* | (2006.01) |
| *C07J 31/00* | (2006.01) |
| *C07J 9/00* | (2006.01) |
| *C07J 41/00* | (2006.01) |

(52) U.S. Cl.
CPC ................ *C07J 31/006* (2013.01); *C07J 9/005* (2013.01); *C07J 41/0061* (2013.01)

(58) Field of Classification Search
CPC .................................................... A61K 31/575
USPC ................................................... 514/182
See application file for complete search history.

(56) References Cited

U.S. PATENT DOCUMENTS

| | | | |
|---|---|---|---|
| 4,892,868 A | 1/1990 | Castagnola et al. |
| 4,921,848 A | 5/1990 | Frigerio et al. |
| 5,061,701 A | 10/1991 | Pellicciari et al. |
| 5,128,481 A | 7/1992 | Oda et al. |
| 5,175,320 A | 12/1992 | Pellicciari et al. |
| 6,200,998 B1 | 3/2001 | Sahoo et al. |
| 6,559,188 B1 | 5/2003 | Gatlin et al. |
| 6,639,078 B1 | 10/2003 | Haffner et al. |
| 6,777,446 B2 | 8/2004 | Houze et al. |
| 6,906,057 B1 | 6/2005 | Forman et al. |
| 6,984,650 B2 | 1/2006 | Haffner et al. |
| 6,987,121 B2 | 1/2006 | Kliewer et al. |
| 7,138,390 B2 | 11/2006 | Pellicciari |
| 2002/0094977 A1 | 7/2002 | Robl et al. |
| 2002/0120137 A1 | 8/2002 | Houze et al. |
| 2002/0132223 A1 | 9/2002 | Forman et al. |
| 2003/0130296 A1 | 7/2003 | Bauer et al. |

FOREIGN PATENT DOCUMENTS

| | | |
|---|---|---|
| EP | 0101554 A1 | 2/1984 |
| EP | 0124068 A1 | 11/1984 |
| EP | 0135782 A2 | 4/1985 |
| EP | 0186023 A2 | 7/1986 |
| EP | 0312867 A1 | 4/1989 |
| EP | 0393493 A2 | 10/1990 |
| EP | 1378749 A1 | 1/2004 |
| EP | 1473042 A1 | 11/2004 |
| EP | 1568706 A1 | 8/2005 |
| EP | 1947108 A1 | 7/2008 |
| WO | WO-9728149 A1 | 8/1997 |
| WO | WO-9731907 A1 | 9/1997 |
| WO | WO-9736579 A1 | 10/1997 |
| WO | WO-9802159 A1 | 1/1998 |
| WO | WO-9938845 A1 | 8/1999 |
| WO | WO-0025134 A1 | 5/2000 |
| WO | WO-0037077 A1 | 6/2000 |
| WO | WO-0040965 A1 | 7/2000 |
| WO | WO-0057915 A1 | 10/2000 |

(Continued)

OTHER PUBLICATIONS

Aldini et al. "Relationship Between Structure and Intestinal Absorption of Bile Acids with a Steroid or Side-Chain Modification." *Steroids.* 61.10(1996):590-597.

(Continued)

*Primary Examiner* — Barbara P Badio
(74) *Attorney, Agent, or Firm* — Ivor Elrifi; Cooley, LLP

(57) ABSTRACT

The invention relates to compounds of Formula A:

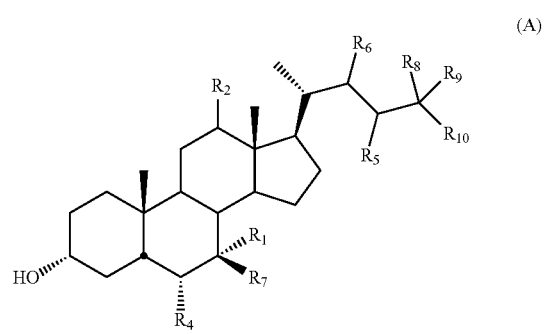

or a pharmaceutically acceptable salt, solvate, hydrate, or prodrug thereof. The compounds of Formula A are TGR5 modulators useful for the treatment of various diseases, including obesity, insulin sensitivity, inflammation, cholestasis, and bile desaturation.

17 Claims, No Drawings

(56) References Cited

FOREIGN PATENT DOCUMENTS

| | | |
|---|---|---|
| WO | WO-0076523 A1 | 12/2000 |
| WO | WO-0130343 A1 | 5/2001 |
| WO | WO-0220463 A2 | 3/2002 |
| WO | WO-02064125 A2 | 8/2002 |
| WO | WO-02072598 A1 | 9/2002 |
| WO | WO-03015771 A1 | 2/2003 |
| WO | WO-03015777 A1 | 2/2003 |
| WO | WO-03016280 A1 | 2/2003 |
| WO | WO-03016288 A1 | 2/2003 |
| WO | WO-03030612 A2 | 4/2003 |
| WO | WO-03043581 A2 | 5/2003 |
| WO | WO-03080803 A2 | 10/2003 |
| WO | WO-03086303 A2 | 10/2003 |
| WO | WO-03090745 A1 | 11/2003 |
| WO | WO-2004007521 A2 | 1/2004 |
| WO | WO-2004048349 A1 | 6/2004 |
| WO | WO-2005032549 A1 | 4/2005 |
| WO | WO-2005082925 A2 | 9/2005 |
| WO | WO-2005089316 A2 | 9/2005 |
| WO | WO-2006122977 A2 | 11/2006 |
| WO | WO-2008002573 A2 | 1/2008 |
| WO | WO-2008091540 A2 | 7/2008 |
| WO | WO-2010059853 A1 | 5/2010 |

OTHER PUBLICATIONS

Bishop-Bailey et al. "Expression and Activation of the Farnesoid X Receptor in the Vasculature." *PNAS*. 101.10(2004):3668-3673.

Center et al. "Chronic Liver Disease: Current Concepts of Disease Mechanisms." *J. Small Anim. Pract.* 40.3(1999):106-114.

Clerici et al. "Effect of Intraduodenal Administration of 23-Methyl-UDCA Diastereoisomers on Bile Flow in Hamsters." *Dig. Dis. Sci.* 37.5(1992):791-798.

Downes et al. "A Chemical, Genetic, and Structural Analysis of the Nuclear Bile Acid Receptor FXR." *Mol. Cell*. 11.4(2003):1079-1092.

Fiorucci et al. "The Nuclear Receptor SHP Mediates Inhibition of Hepaptic Stellate Cells by FXR and Protects Against Liver Fibrosis." *Gastroenterol*. 127(2004):1497-1512.

Forman et al. "Identification of a Nuclear Receptor that is Activated by Farnesol Metabolites." *Cell*. 81(1995):687-693.

Fukuchi et al. "5β-Cholane Activators of the Farnesoid X Receptor." *J. Steroid Biochem. Mol. Biol.* 94.4(2005):311-318.

Haslewood et al. "Specificity and some characteristics of a 7.alpha.-hydroxysteroid dehydrogenase from *E. coli*." Datebase CA [online], Database accession No. 1978 : 419015. (1975).

Honorio et al. "Hologram QSAR Studies on Farnesoid X Receptor Activators." *Lett. Drug Des. Dis.* 3.4(2006):261-267.

Kihira et al. "Synthesis of Sulfonate Analogs of Bile Acids." *Steroids*. 57.4(1992):193-198.

Kim et al. "Hypocholesterolemic Effect of Bile Acid Sulfonate Analogs in Hamsters." *Biol. Phami. Bull.* 24.3(2001):218-220.

Kliewer et al. "Peroxisome Proliferator-Activated Receptors: From Genes to Physiology." *Endo J.* 56(2001):239-263.

Kuroki et al. "7-Methyl Bile Acids: 7 β-methyl-cholic Acid Inhibits Bacterial 7-dehydroxylation of Cholic Acid and Chenodeoxycholic Acid in the Hamster." *J. Lipid Res.* 28.7(1987):856-863.

Kuroki et al. "Synthesis of Potential Cholelitholytic Agents: 3α, 7α, 12α-trihydroxy-7β-methyl- 5β-Cholanoic Acid, 3α, 7β, 12α-trihydroxy-7α-methyl-5β-cholanoic Acid, and 3α, 12α, dihydroxy-7ε-methyl-5α-cholanoic Acid." *J. Lipid Res.* 26(1985):1205-1211.

Kuroki. "Metabolism of the Bile Acid Analogues 7 β-,ethyl-Cholic Acid and 7 α-Methyl-Ursocholic Acid." *Gastroenterol*. 92.4(1987):876-884.

Liu et al. "Hepatoprotection by the Farnesoid X Receptor Agonist GW4064 in Rat Models of Intra- and Extrahepatic Cholestasis." *J. Clin. Invest.* 112.11(2003):1678-1687.

Mangelsdorf et al. "The RXR Heterodimers and Orphan Receptors." *Cell*. 83(1995):841-850.

Mi et al. "Structural Basis for Bile Acid Binding and Activation of the Nuclear Receptor FXR." *Mol. Cell*. 11(2003):1093-1100.

Mikami et al. "Effect of Some Sulfonate Analogues of Ursodeoxycholic Acid on Biliary Lipid Secretion in the Rat." *J. Lipid Res.* 37.6(1996):1181-1188.

Miki et al. "Sulfonate Analogues of Chenodeoxycholic Acid: Metabolism of Sodium 3α7α- dihydroxy-25- homo-5β-cholane-25-sulfonate and Sodium 3α,7α-dihydroxy-24-nor-5β- cholane-23-sulfonate in the Hamster." *J. Lipid Res.* 33.11(1992):1629-1637.

Nesto et al. "Thiazolidinedione Use, Fluid Retention, and Congestive Heart Failure." *Diabetes Care*. 27.1(2004):256-263.

Pellicciari et al. "Discovery of 6α-Ethyl-23(S)-methylcholic Acid (S-EMCA, INT-777) as a Potent and Selective Agonist for the TGR5 Receptor, a Novel Target for Diabesity." *J. Med. Chem.* 52(2009):7958-7961.

Pellicciari et al. "6α-Ethyl-Chenodeoxycholic Acid (6-ECDCA), a Potent and Selective FXR Agonist Endowed with Anticholestatic Activity." *J. Med. Chem.* 45.17(2002):3569-3572.

Pellicciari et al. "Bile Acid Derivatives as Ligands of the Farnesoid X Receptor. Synthesis, Evaluation, and Structure-Activity Relationship of a Series of Body and Side Chain Modified Analogues of Chenodeoxycholic Acid." *J. Med. Chem.* 47(2004):4559-4569.

Pellicciari et al. "Nongenomic Actions of Bile Acids. Synthesis and Preliminary Characterization of 23- and 6,23-Alkyl-Substituted Bile Acid Derivatives as Selective Modulators for the G-Protein Coupled Receptor TGR5." *J. Med. Chem.* 50(2007):4265-4268.

Raskin et al. "A Randomized Trial of Rosiglitazone Therapy in Patients With Inadequately Controlled Insulin-Treated Type 2 Diabetes." *Diabetes Care*. 24.7(2001):1226-1232.

Roda et al. "23-Methyl-3α,7β-dihydroxy-5β-cholan-24-oic Acid: Dose-Response Study of Biliary Secretion in Rat." *Hepatol*. 8.6(1988):1571-1576.

Roda et al. "Bile Acids With a Cyclopropyl-Containing Side Chain. IV. Physicochemical and Biological Properties of the Four Diastereoisomers of 3α, 7β-dihydroxy-22,23-methylene-5β-cholan-24-oic Acid." *J. Lipid Res.* 28.12(1987):1384-1397.

Rubin et al. "Combination Therapy With Pioglitazone and Insulin in Patients With Type 2 Diabetes." *Diabetes*. 48(S1)(1999):A110. (Abstract Only).

Sato et al. "Novel Potent and Selective Bile Acid Derivatives as TGR5 Agonists: Biological Screening, Structure-Activity Relationships, and Molecular Modeling Studies." *J. Med. Chem.* 51.6(2008):1831-1841.

Schmider et al. "Evidence for an additional sinusoidal bile salt transport system." Datebase CA [online], Database accession No. 2000 : 260886. (1999).

Souillac et al. "Characterization of Delivery Systems, Differential Scanning Calorimetry." *Encyclopedia of Controlled Drug Delivery*. John Wiley & Sons. (1999):212-227.

Stenner et al. "The Effect of Ursodeoxycholic Acid on Fibrosis Markers in Alcoholic Liver Disease." *Flak Symposium*. (2002):229-235.

Une et al. "New bile acid analogs: 3α, 7α-dihydroxy-7β-methyl-5β-cholanoic acid, 3α, 7β-dihydroxy-7α-methyl-5β-cholanoic acid, and 3α-hydroxy-7ε-methyl-5β-cholanoic acid." *J. Lipid Res.* 25(1984):407-410.

Urizar et al. "A Natural Product that Lowers Cholesterol as an Antagonist Ligand for FXR." *Science*. 296.5573(2002):1703-1706.

Vippagunta et al. "Crystalline Solids." *Adv. Drug Del. Rev.* 48(2001):3-26.

Willson et al. "The PPARs: From Orphan Receptors to Drug Discovery." *J. Med. Chem.* 43.4(2000):527-550.

Susumu Katsuma, et al. "Bile acids promote glucagon-like peptide-1 secretion through TGR5 in a murine enteroendocrine cell line STC-1", Biochemical and Biophysical Research Communications 329 (2005) 386-390.

Máire E. Doyle, et al., Mechanisms of Action of GLP-1 in the Pancreas, Pharmacol Ther. Mar. 2007; 113(3): 546-593.

TGR5 MODULATORS AND METHODS OF USE THEREOF

RELATED APPLICATIONS

This application is continuation of U.S. application Ser. No. 12/523,670, filed Apr. 30, 2010, now U.S. Pat. No. 8,410,083, and is a 35 U.S.C. §371 National Phase Application of PCT/US2008/000658, filed Jan. 18, 2008, which claims priority from EP07001143.2, filed Jan. 19, 2007 and EP07012079.5, filed Jun. 20, 2007, each of which is incorporated by reference in its entirety.

FIELD OF THE INVENTION

The invention concerns relates to compounds that modulate TGR5 and compositions useful in methods for the treatment and/or prevention of various diseases.

BACKGROUND OF THE INVENTION

TGR5 receptor is a G-protein-coupled receptor that has been identified as a cell-surface receptor that is responsive to bile acids. The primary structure of TGR5 and its responsiveness to bile acids has been found to be highly conserved in TGR5 among human, bovine, rabbit, rat, and mouse, and thus suggests that TGR5 has important physiological functions. TGR5 has been found to be widely distributed in not only lymphoid tissues but also in other tissues. High levels of TGR5 mRNA have been detected in placenta, spleen, and monocytes/macrophages. Bile acids have been shown to induce internalization of the TGR5 fusion protein from the cell membrane to the cytoplasm. Kawamata et al. 2003, J. Bio. Chem., 278, 9435. TGR5 has been found to be identical to hGPCR19 reported by Takeda et al. 2002, FEBS Lett. 520, 97-101.

Bile acids are cholesterol metabolites that are formed in the liver and secreted into the duodenum of the intestine. Bile acids are compounds that play essential roles in the absorption of dietary lipids and regulation of bile acid synthesis. For example, Farnesoid X receptor (FXR) and pregnane X receptor (PXR) have recently been identified as specific nuclear receptors for bile acids. Through activation of FXR, bile acids repress the expression of the rate-limiting enzyme in bile acid synthesis, cholesterol 7a-hydroxylase (Cyp7a). The activation of PXR by bile acids results in both the repression of Cyp7a and the transcriptional induction of the bile acid-metabolizing enzyme, cytochrome P450 3a. At high concentrations, bile acids are also known to exhibit immunosuppressive effects on cell-mediated immunity and macrophage functions. Bile acids including deoxycholic acid (DCA) and chenodeoxycholic acid (CDCA) have been demonstrated to have inhibitory activities on the lipopolysaccharide (LPS)-induced promotion of cytokines in macrophages, including interleukin (IL)-1, IL-6, and tumor necrosis factor alpha (TNFα).

Bile acid compounds that modulate TGR5 have been used for the treatment of various diseases, including central nervous diseases as well as inflammatory diseases (WO 01/77325 and WO 02/84286). Specifically, bile acid compounds alkylated in position 6 of cholanic acid have been disclosed in WO 02/072598, WO 2004/0007521, and EP 1568706 as FXR agonists. The bile acid compound, 23-methyl-ursodeoxycholic (3-alpha,7-beta-dihydroxy-5-beta-cholan-24-oic acid) has also been disclosed (Hepatology, 1988, 8(6), 1571-1576) for the treatment of cholestatic liver diseases.

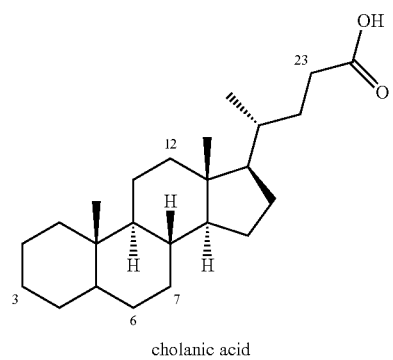

cholanic acid

Modulators of TGR5 provide methods of regulating bile acid and cholesterol homeostasis, fatty acid absorption, and protein and carbohydrate digestion. There is a need for the development of TGR5 modulators for the treatment and/or prevention of various diseases. The present invention has identified compounds that modulate TGR5 as well as methods of using these compounds to treat disorders such as central nervous system diseases, inflammatory diseases, and metabolic diseases such as obesity and insulin sensitivity. Methods of using the compounds of the invention also include to prevent disorders such as central nervous diseases, inflammatory diseases, and metabolic diseases e.g., metabolic syndrome, Type 2 diabetes, obesity, etc.

SUMMARY OF THE INVENTION

The present invention relates to TGR5 modulators and their use to treat and/or prevent various diseases.

In one aspect, the invention relates to a compound of formula A:

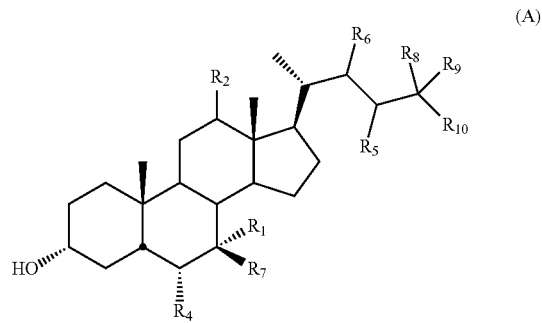

(A)

or a pharmaceutically acceptable salt, solvate, hydrate, or prodrug thereof, wherein: $R_1$ is hydrogen, hydroxy, substituted or unsubstituted alkyl, or halogen; $R_2$ is hydrogen or α-hydroxy; $R_3$ is hydrogen, hydroxy, $NH(CH_2)_mSO_3H$, or $NH(CH_2)_nCO_2H$; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; $R_8$ is hydrogen, substituted or unsubstituted alkyl; $R_9$ is hydrogen, substituted or unsubstituted alkyl or taken together $R_8$ and $R_9$ form a carbonyl; $R_{10}$ is $R_3$, $SO_3H$; m is an integer 0, 1, 2, 3, 4, or 5; and n is an integer 0, 1, 2, 3, 4, or 5. In one aspect, when $R_5$ is methyl, $R_1$ is hydroxyl, and $R_3$ is hydroxyl or $NHCH_2CH_2SO_3H$, then $R_4$ is not hydrogen.

In one aspect of the invention, $R_1$ is hydrogen or hydroxy. $R_1$ is hydroxy. $R_1$ is hydrogen. $R_2$ is α-hydroxy. $R_1$ is hydroxy and $R_2$ is α-hydroxy. $R_1$ is hydroxy and $R_2$ is H. $R_1$ is hydroxy and $R_2$ is H. At least one of $R_1$ or $R_2$ is hydroxy. At least one of $R_1$ or $R_2$ is hydrogen. $R_1$ and $R_2$ are the same. $R_1$ and $R_2$ are each α-hydroxy. $R_1$ and $R_2$ are each hydrogen.

In another aspect of the invention, $R_{10}$ is $R_3$. $R_3$ is hydroxyl, $NH(CH_2)_mSO_3H$, or $NH(CH_2)_nCO_2H$. $R_3$ is hydroxyl. $R_3$ is not hydroxyl. $R_3$ is $NH(CH_2)_mSO_3H$. $R_3$ is $NH(CH_2)_mSO_3H$ and m is 2. $R_3$ is $NH(CH_2)_nCO_2H$. $R_3$ is $NH(CH_2)_nCO_2H$ and n is 1.

In another aspect of the invention, $R_4$ is hydrogen or unsubstituted alkyl. $R_4$ is hydrogen.
$R_4$ is unsubstituted alkyl. $R_4$ is unsubstituted alkyl. $R_4$ is methyl or ethyl. $R_4$ is methyl. $R_4$ is ethyl. $R_3$ and $R_4$ are the same. $R_3$ and $R_4$ are different. $R_3$ and $R_4$ are each hydrogen. $R_3$ is hydroxyl and $R_4$ is hydrogen. $R_3$ is $NH(CH_2)_mSO_3H$ and $R_4$ is hydrogen. $R_3$ is $NH(CH_2)_mSO_3H$, $R_4$ is hydrogen, and m is 2. $R_3$ is $NH(CH_2)_nCO_2H$ and $R_4$ is hydrogen. $R_3$ is $NH(CH_2)_nCO_2H$, $R_4$ is hydrogen, and n is 1. $R_3$ is H and $R_4$ is unsubstituted alkyl. $R_3$ is OH and $R_4$ is methyl. $R_3$ is OH and $R_4$ is ethyl. $R_3$ is OH and $R_4$ is methyl.

In another aspect, $R_5$ is unsubstituted or substituted alkyl. $R_5$ is in the S-configuration. $R_5$ is in the R-configuration. $R_5$ is methyl or ethyl. $R_5$ is S-methyl. $R_5$ is R-methyl. $R_5$ is S-ethyl. $R_5$ is R-ethyl. $R_5$ is substituted alkyl substituted with phenyl. $R_5$ is benzyl. $R_5$ is S-benzyl. $R_5$ is R-benzyl. $R_5$ is aryl. $R_5$ is phenyl. $R_4$ and $R_5$ are each unsubstituted alkyl. $R_4$ and $R_5$ are each unsubstituted alkyl, wherein $R_5$ is in the S-configuration and $R_4$ is in the alpha-configuration. $R_4$ and $R_5$ are each unsubstituted alkyl and $R_1$ is hydroxy. $R_4$ and $R_5$ are each unsubstituted alkyl and $R_2$ is hydrogen. $R_4$ and $R_5$ are each unsubstituted alkyl, $R_1$ is hydroxy, and $R_2$ is hydrogen.

In one aspect of the invention, $R_1$, $R_2$, $R_3$, and $R_4$ are hydrogen. $R_2$, $R_3$, and $R_4$ are hydrogen. $R_2$ and $R_3$ are hydrogen. At least one of $R_1$, $R_2$, $R_3$, or $R_4$ is hydrogen. At least two of $R_1$, $R_2$, $R_3$, or $R_4$ are hydrogen. At least three of $R_1$, $R_2$, $R_3$, or $R_4$ are hydrogen. $R_1$, $R_2$, $R_3$, and $R_4$ are hydrogen.

In one aspect of the invention, $R_1$, $R_2$, and $R_4$ are hydrogen and $R_3$ is OH. $R_2$ and $R_4$ are hydrogen and $R_3$ is OH. $R_2$ is hydrogen and $R_3$ is OH. At least one of $R_1$, $R_2$, or $R_4$ is hydrogen and $R_3$ is OH. At least two of $R_1$, $R_2$, or $R_4$ are hydrogen and $R_3$ is OH. All of $R_1$, $R_2$, and $R_4$ are hydrogen and $R_3$ is OH. $R_1$, $R_2$ and $R_4$ are hydrogen and $R_3$ is OH.

In another aspect of the invention, at least one of $R_1$ or $R_7$ is unsubstituted alkyl. At least one of $R_1$ or $R_7$ is methyl. At least one of $R_1$ or $R_7$ is ethyl. At least one of $R_1$ or $R_7$ is propyl. $R_1$ is methyl. $R_1$ is ethyl. $R_1$ is propyl. $R_7$ is methyl. $R_7$ is ethyl. $R_7$ is propyl. Both $R_1$ and $R_7$ are unsubstituted alkyl. Both $R_1$ and $R_7$ are methyl. Both $R_1$ and $R_7$ are ethyl. $R_7$ is hydrogen. $R_7$ is hydroxy. $R_1$ is hydrogen. $R_1$ is hydroxyl. One of $R_1$ or $R_7$ is unsubstituted alkyl and the other $R_1$ or $R_7$ is hydrogen. One of $R_1$ or $R_7$ is unsubstituted alkyl and the other $R_1$ or $R_7$ is hydroxy. At least one of $R_1$ or $R_7$ is unsubstituted alkyl and $R_5$ is unsubstituted or substituted alkyl. At least one of $R_1$ or $R_7$ is methyl and $R_5$ is methyl. $R_7$ is hydroxy and both $R_1$ and $R_5$ are unsubstituted alkyl. $R_1$ is hydroxyl and both $R_7$ and $R_5$ are unsubstituted alkyl. At least one of $R_1$ or $R_7$ is unsubstituted alkyl and $R_5$ is unsubstituted or substituted alkyl, further wherein $R_5$ is in the S-configuration. At least one of $R_1$ or $R_7$ is unsubstituted alkyl and $R_5$ is unsubstituted or substituted alkyl, further wherein $R_5$ is in the R-configuration.

In another aspect, $R_1$ is hydroxy and $R_7$ is methyl. $R_1$ is methyl and $R_7$ is hydroxy. $R_6$ is unsubstituted alkyl. $R_6$ is methyl. $R_6$ is ethyl. $R_6$ is propyl.

In another aspect, $R_8$ is hydrogen. $R_8$ is unsubstituted alkyl. $R_8$ is methyl. $R_8$ is ethyl. $R_8$ is propyl. $R_2$ is α-hydroxy and $R_8$ is unsubstituted alkyl. In another aspect, $R_8$ and $R_9$ form a carbonyl.

In one aspect, $R_{10}$ is $R_3$. $R_3$ is hydroxyl. At least one of $R_8$ or $R_9$ is hydrogen. $R_8$ and $R_9$ are both hydrogen. At least one of $R_8$ or $R_9$ is unsubstituted alkyl. At least one of $R_8$ or $R_9$ is methyl. At least one of $R_8$ or $R_9$ is ethyl. In another aspect, $R_{10}$ is $SO_3H$.

In another aspect of the present invention, when $R_2$, $R_4$, and $R_6$ are each hydrogen, $R_3$ is hydroxyl, and one of $R_1$ and $R_7$ is hydrogen or hydroxyl, then the other $R_1$ or $R_7$ is not methyl. In another aspect, when $R_2$ is α-OH; $R_3$ is hydroxyl; $R_4$ and $R_6$ are each hydrogen; and one of $R_1$ and $R_7$ is hydrogen or hydroxyl, then the other $R_1$ or $R_7$ is not methyl. In another aspect, the present invention does not include the following compounds: 3α,7α-dihydroxy-7β-methyl-5β-cholanoic acid, 3α,7β-dihydroxy-7α-methyl-5β-cholanoic acid, 3α-hydroxy-7ε-methyl-5β-cholanoic acid, 3α,7β,12α-trihydroxy-7α-methyl-5β-cholan-24-oic acid; 3α,7α,12α-trihydroxy-7β-methyl-5β-cholan-24-oic acid; and 3α,12α-dihydroxy-7ε-methyl-5β-cholan-24-oic acid.

In another aspect of the present invention, when $R_3$ is hydroxyl and one of $R_1$ and $R_7$ is methyl and the other $R_1$ and $R_7$ is hydrogen or hydroxyl, then $R_2$, $R_4$, and $R_6$ are not all hydrogen. In another aspect, when $R_2$ is α-OH, $R_3$ is hydroxyl, and one of $R_1$ and $R_7$ is methyl and the other $R_1$ and $R_7$ is hydrogen or hydroxyl, then $R_4$ and $R_6$ are not all hydrogen.

The invention includes a method of treating disease in a subject, comprising administering a compound of formula A to a subject in need thereof. The invention includes use of a compound of formula A or a pharmaceutically acceptable salt, solvate, hydrate, or prodrug thereof, in the preparation of a medicament for treating and/or preventing disease involving the modulation of the TGR5 receptor comprising administering said compound to a subject in need thereof. The invention includes a composition comprising a compound of formula A or a pharmaceutically acceptable salt, solvate, hydrate, or prodrug thereof, and at least one pharmaceutically acceptable excipient.

In one aspect the invention relates to a compound of formula I:

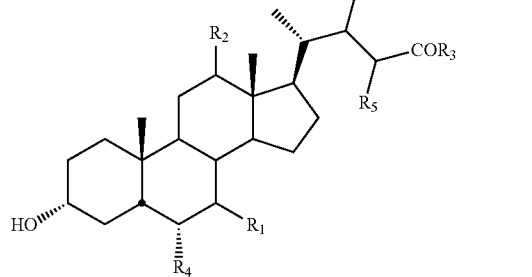

or a pharmaceutically acceptable salt, solvate, hydrate, or prodrug thereof, wherein $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, unsubstituted or substituted alkyl, or halogen; $R_5$ is unsubstituted or substituted alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5; and n is an integer 0, 1, 2, 3, 4, or 5. In one aspect, when $R_5$ is methyl, $R_1$ is hydroxyl, and $R_3$ is hydroxyl or $NHCH_2CH_2SO_3H$, then $R_4$ is not hydrogen.

In one aspect of the present invention, $R_1$ is hydrogen or hydroxy. $R_1$ is α-hydroxy. $R_1$ is β-hydroxy. $R_2$ is α-hydroxy. $R_1$ is β-hydroxy and $R_2$ is α-hydroxy. $R_1$ is β-hydroxy and $R_2$ is H. $R_1$ is α-hydroxy and $R_2$ is H. $R_1$ and $R_2$ are each α-hydroxy. $R_1$ and $R_2$ are each hydrogen.

In another aspect of the present invention, $R_3$ is hydrogen, hydroxyl, $NH(CH_2)_mSO_3H$, or $NH(CH_2)_nCO_2H$. $R_3$ is hydroxyl. $R_3$ is not hydroxyl. $R_3$ is $NH(CH_2)_mSO_3H$. $R_3$ is $NH(CH_2)_mSO_3H$ and m is 2. $R_3$ is $NH(CH_2)_nCO_2H$. $R_3$ is $NH(CH_2)_nCO_2H$ and n is 1.

In another aspect of the present invention, $R_4$ is hydrogen or unsubstituted alkyl. $R_4$ is hydrogen. $R_4$ is unsubstituted alkyl. $R_4$ is methyl or ethyl. $R_3$ and $R_4$ are the same. $R_3$ and $R_4$ are different. $R_3$ and $R_4$ are each hydrogen. $R_3$ is hydroxyl and $R_4$ is hydrogen.

In another aspect of the present invention, $R_3$ is $NH(CH_2)_mSO_3H$ and $R_4$ is hydrogen. $R_3$ is $NH(CH_2)_mSO_3H$, $R_4$ is hydrogen and m is 2. $R_3$ is $NH(CH_2)_nCO_2H$ and $R_4$ is hydrogen. $R_3$ is $NH(CH_2)_nCO_2H$ and $R_4$ is hydrogen and n is 1. $R_3$ is OH and $R_4$ is alkyl. $R_3$ is OH and $R_4$ is unsubstituted alkyl. $R_3$ is OH and $R_4$ is methyl.

In another aspect of the present invention, $R_5$ is unsubstituted or substituted alkyl. $R_5$ is in the S-configuration. $R_5$ is in the R-configuration. $R_5$ is methyl or ethyl. $R_5$ is S-methyl. $R_5$ is R-methyl. $R_5$ is S-ethyl. $R_5$ is R-ethyl. $R_5$ is alkyl substituted with aryl. $R_5$ is alkyl substituted with phenyl. $R_5$ is benzyl. $R_5$ is S-benzyl. $R_5$ is R-benzyl. $R_5$ is aryl. $R_5$ is phenyl.

In another aspect of the present invention, $R_4$ and $R_5$ are each unsubstituted alkyl. $R_4$ and $R_5$ are each unsubstituted alkyl and $R_5$ is in the S-configuration. $R_4$ is unsubstituted alkyl and $R_5$ is substituted alkyl. $R_4$ and $R_5$ are each unsubstituted alkyl and $R_1$ is α-hydroxy. $R_4$ and $R_5$ are each unsubstituted alkyl and $R_2$ is hydrogen. $R_4$ and $R_5$ are each unsubstituted alkyl, $R_1$ is α-hydroxy, and $R_2$ is hydrogen.

In another aspect of the present invention, $R_1$, $R_2$, $R_3$, and $R_4$ are hydrogen. $R_2$, $R_3$, and $R_4$ are hydrogen. $R_2$ and $R_3$ are hydrogen. $R_1$, $R_2$, and $R_4$ are hydrogen and $R_3$ is OH.

In another aspect of the present invention, at least one of $R_1$, $R_2$, $R_3$, or $R_4$ is hydrogen. At least two of $R_1$, $R_2$, $R_3$, or $R_4$ are hydrogen. At least three of $R_1$, $R_2$, $R_3$, or $R_4$ are hydrogen. $R_1$, $R_2$, $R_3$, and $R_4$ are hydrogen.

In another aspect of the present invention, at least one of $R_1$, $R_2$, or $R_4$ is hydrogen and $R_3$ is OH. At least two of $R_1$, $R_2$, or $R_4$ are hydrogen and $R_3$ is OH. All of $R_1$, $R_2$, and $R_4$ are hydrogen and $R_3$ is OH.

Another aspect of the present invention includes a composition or medicament comprising a compound of formula I.

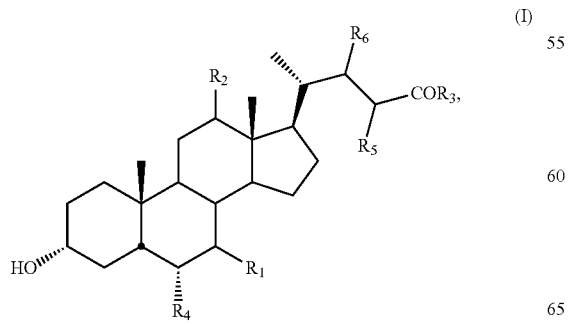

(I)

or a pharmaceutically acceptable salt, solvate, hydrate, or prodrug thereof, and at least one pharmaceutically acceptable excipient wherein $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, unsubstituted alkyl, or halogen; $R_5$ is unsubstituted or substituted alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5; and n is an integer 0, 1, 2, 3, 4, or 5. In one aspect the present invention includes a composition or medicament comprising a compound of formula I with the proviso that when $R_5$ is methyl, $R_1$ is hydroxyl, and $R_3$ is hydroxyl or $NHCH_2CH_2SO_3H$, then $R_4$ is not hydrogen.

Another aspect of the present invention includes a method of treating disease in a subject, comprising administering a therapeutically effective amount of a compound of formulae I, IA, II, and A to a subject in need thereof. Another aspect of the present invention includes a method of preventing disease in a subject comprising administering a prophylactically effective amount of a compound of formulae I, IA, II, and A to a subject in need thereof. The present invention includes treatment and/or prevention of diseases that involves modulation of TGR5 receptor. The present invention includes use of a compound of formulae A, I, IA, and II in preparation of a medicament for treating and/or preventing a disease that involves the modulation of TGR5 receptor. In one aspect, the disease is a metabolic disease, including obesity and insulin sensitivity. In another aspect, the disease is inflammatory disease, including rheumatoid arthritis and allergy. In another aspect, the disease is cholestasis or bile desaturation. The present invention includes where the subject is human.

The present invention also relates to compounds of formula IA and II:

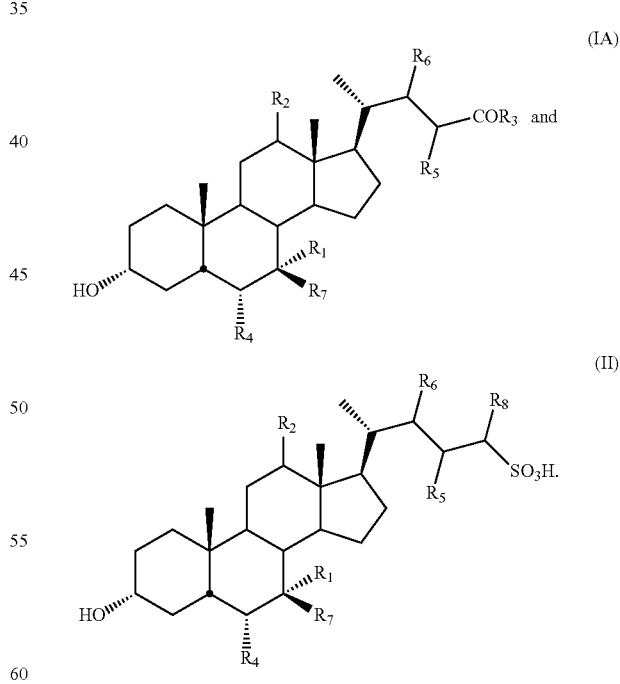

$R_1$, $R_2$, $R_3$, $R_4$, $R_5$, $R_6$, $R_7$, and $R_8$ for the above formula IA and $R_1$, $R_2$, $R_4$, $R_5$, $R_6$, $R_7$, and $R_8$ for the above formula II are as described below. The present invention relates to a composition or medicament of a compound of formulae IA or formula II. The present invention includes use of a compound of formulae I, IA, A, and II in the manufacture of a composition for medicament for the treatment and/or prevention of a disease state involving modulation of TGR5.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DESCRIPTION OF THE INVENTION

The details of one or more embodiments of the invention are set forth in the accompanying description below. Although any methods and materials similar or equivalent to those described herein can be used in the practice or testing of the present invention, the methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present specification will control.

DEFINITIONS

For convenience, certain terms used in the specification, examples and appended claims are collected here.

The term "treating", as used herein, means relieving, lessening, reducing, eliminating, modulating, or ameliorating, i.e. causing regression of the disease state or condition.

The term "preventing", as used herein means, to completely or almost completely stop a disease state or condition, from occurring in a patient or subject, especially when the patient or subject is predisposed to such or at risk of contracting a disease state or condition. Preventing can also include inhibiting, i.e. arresting the development, of a disease state or condition, and relieving or ameliorating, i.e. causing regression of the disease state or condition, for example when the disease state or condition may already be present.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has six or fewer carbon atoms in its backbone (e.g., $C_1$-$C_6$ for straight chain, $C_3$-$C_6$ for branched chain). In some examples, a straight chain or branched chain alkyl has four or fewer carbon atoms in its backbone. Further, cycloalkyls have from three to eight carbon atoms in their ring structure.

The term "substituted alkyl" refers to an alkyl moieties having a substituent replace one or more hydrogen atoms on at least one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at least one ring position with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

Unless the number of carbons is otherwise specified, "lower alkyl" includes an alkyl group, as defined above, but having from one to ten, for example, from one to six, carbon atoms in its backbone structure.

The term "alkoxy" or "alkoxyl" includes alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

An "anionic group," as used herein, refers to a group that is negatively charged at physiological pH. Anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19-23). Another anionic group is a carboxylate.

The term "unstable functionality" refers to a substitution pattern that contains a labile linkage, e.g., a functionality or bond that is susceptible to hydrolysis or cleavage under physiological conditions (e.g., aqueous solutions in the neutral pH range). Examples of unstable functionalities include acetals and ketals.

The terms "crystal polymorphs" or "polymorphs" refer to the existence of more than one crystal form for a compound, salt or solvate thereof. Crystal polymorphs of the bile acid analog compounds are prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

It will be noted that the structure of some of the compounds of the invention include asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Enantiomers (R- and S-configurations) are named according to the system developed by R. S. Cahn, C. Ingold, and V. Prelog.

Further, the structures and other compounds discussed in this application include all atropic isomers thereof. Atropic isomers are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Stable compound" and "stable structure" are meant to indicate a compound that is sufficiently robust to survive isolation to a useful degree of purity from a reaction mixture, and formulation into an efficacious therapeutic agent.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

As defined herein, the term "derivative", e.g., in the term "bile acid derivatives", refers to compounds that have a common core 4-membered ring structure, and are substituted with various groups as described herein.

The term "bioisostere" refers to a compound resulting from the exchange of an atom or of a group of atoms with another, broadly similar, atom or group of atoms. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

"Combination therapy" (or "co-therapy") includes the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The terms "parenteral administration" and "administered parenterally" as used herein refer to modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "pulmonary" as used herein refers to any part, tissue or organ whose primary function is gas exchange with the external environment, e.g., $O_2/CO_2$ exchange, within a patient. "Pulmonary" typically refers to the tissues of the respiratory tract. Thus, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli). For purposes of the present invention, "pulmonary" also includes a tissue or cavity that is contingent to the respiratory tract, in particular, the sinuses.

The term "effective amount" means a "therapeutically effective amount" and/or a "prophylatically effective amount."

A "therapeutically effective amount" of a compound of the invention, or a combination of compounds is an amount (quantity or concentration) of compound or compounds. In one embodiment, when a therapeutically effective amount of a compound is administered to a subject in need of treatment symptoms arising from the disease are ameliorated immediately or after administration of the compound one or more times. The amount of the compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "prophylactically effective amount" means an amount (quantity or concentration) of a compound of the present invention, or a combination of compounds, that is administered to prevent or reduce the risk of a disease—in other words, an amount needed to provide a preventative or prophylactic effect. The amount of the present compound to be administered to a subject will depend on the particular disorder, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors.

The term "reducing the risk of", as used herein, means to lower the likelihood or probability of a central nervous system disease, inflammatory disease and/or metabolic disease from occurring in a patient, especially when the patient or subject is predisposed to such occurrence.

A "pharmaceutically acceptable salt" or "salt" of a compound of the invention is a product of the compound that contains an ionic bond, and is typically produced by reacting the compound with either an acid or a base, suitable for administering to a subject.

A "composition" is a formulation containing s compound of the invention in a form suitable for administration to a subject. In another embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In another embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). Typically, the subject is human.

Compounds of the invention also include prodrugs or physiologically equivalent derivatives. A "prodrug" or "physiologically equivalent derivative" includes a precursor form of the drug which is metabolically converted in vivo to produce the active drug. The invention further contemplates the use of prodrugs which are converted in vivo to the TGR5 modulating compounds used in the methods of the invention (see, e.g., R. B. Silverman, 1992, "The Organic Chemistry of Drug Design and Drug Action", Academic Press, Chp. 8). Such prodrugs can be used to alter the biodistribution (e.g., to allow compounds which would not typically cross the blood-brain barrier to cross the blood-brain barrier) or the pharmacokinetics of the TGR5 modulating compound. For example, an anionic group, e.g., a carboxylate, sulfate or sulfonate, can be esterified, e.g., with an alkyl group (e.g., a methyl group) or a phenyl group, to yield an ester. When the ester is administered to a subject, the ester is cleaved, enzymatically or non-enzymatically, reductively or hydrolytically, to reveal the anionic group. Such an ester can be cyclic, e.g., a cyclic sulfate or sulfone, or two or more anionic moieties may be esterified through a linking group. An anionic group can be esterified with moieties (e.g., acyloxymethyl esters) which are cleaved to reveal an intermediate TGR5 modulating compound which subsequently decomposes to yield the active TGR5 modulating compound. In one embodiment, the prodrug is a reduced form of a carboxylate, sulfate or sulfonate, e.g., an alcohol or thiol, which is oxidized in vivo to the TGR5 modulating compound. Furthermore, an anionic moiety can be esterified to a group which is actively transported in vivo, or which is selectively taken up by target organs.

As used herein, the term "amino acid conjugates" refers to conjugates of the compounds of formulae I, IA, and A with any suitable amino acid. Taurine ($NH(CH_2)_2SO_3H$) and glycine ($NHCH_2CO_2H$) are examples of amino acid conjugates.

Suitable amino acid conjugates of the compounds of formulae I, IA, and A have the added advantage of enhanced integrity in bile or intestinal fluids. Suitable amino acids are not limited to taurine and glycine. The present invention encompasses amino acid conjugates of the compounds of formulae I, IA, and A.

The term "TGR5 modulator" means any compound that interacts with the TGR5 receptor. The interaction is not limited to a compound acting as an antagonist, agonist, partial agonist, or inverse agonist of the TGR5 receptor. In one aspect, the compounds of the present invention act as an antagonist of the TGR5 receptor. In another aspect, the compounds of the present invention act as an agonist of the TGR5 receptor. In another aspect, the compounds of the present invention act as a partial agonist of the TGR5 receptor. In another aspect, the compounds of the present invention as an inverse agonist of the TGR5 receptor. The profile of a ligand, traditionally, endogenous or synthetic, is characterized by its intrinsic efficacy 'e' originally described by Furchgott in 1966. It is used to express the degree to which the different ligands produce varying biological responses while occupying the same number of receptors. Generally, the term "agonist" means a compound that enhances the activity of another molecule or receptor site. An agonist, by classical definition, whether a orthosteric, allosteric, inverse or a co-agonist has a property to bind to the receptor, alter its receptor state and result in a biological action. Consequently, agonism is defined as a property of an agonist or a ligand to produce a biological action. In contrast to this, an "antagonist" is essentially an agonist with high affinity to the same receptor macromolecule, but with very less or negligible intrinsic efficacy, and thus sterically prevents the biological actions of an agonist. As a property, antagonism may be functional or physiological, where an agonist has a direct competition for the receptor site in former and opposing effects via a different receptor-messenger system in the later. More specifically, a TGR5 agonist is a receptor ligand or compound that binds to TGR5 and increases the concentration of cyclic adenosine monophosphate (cAMP) by at least 20% in cells expressing the receptor." Conversely, a TGR5 antagonist would be a compound that antagonizes or blocks the activity of an agonist, thereby effecting a reduction in the concentration of cAMP.

The term "metabolic disorders" includes but is not limited to dyslipidemia, atherosclerosis, obesity, coronary heart disease, stroke, insulin resistance/sensitivity, and diabetes.

The term "inflammatory disease" means an inflammatory response which causes injury to autologous tissues. Inflammatory diseases include but are not limited to rheumatoid arthritis, osteoarthritis, cervical spondylosis, cumulative trauma disorder, allergy, endometriosis, pelvic inflammatory disease, adhesive peritonitis, appendicitis, pericarditis, and pleuritis.

The present invention relates to compounds having TGR5 receptor modulating activity and their use to treat and/or prevent various diseases including, central nervous system diseases, inflammatory diseases, and metabolic diseases such as obesity and insulin sensitivity. Further, the present invention relates to compounds of formulae A, I, IA, and II. According to one aspect, the present invention provides a compound of formula I:

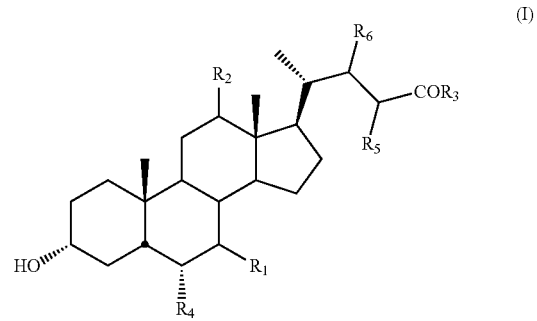

or a pharmaceutically acceptable salt, solvate, hydrate, or prodrug thereof, wherein: $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, unsubstituted or substituted alkyl, or halogen; $R_5$ is unsubstituted or substituted alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5, and n is an integer 0, 1, 2, 3, 4, or 5. In one aspect, when $R_5$ is methyl, $R_1$ is hydroxyl, and $R_3$ is hydroxyl or $NHCH_2CH_2SO_3H$, then $R_4$ is not hydrogen.

In one aspect, the present invention provides compounds where $R_1$ is hydrogen or hydroxy. $R_1$ is hydroxy. $R_1$ is hydrogen. $R_1$ is α-hydroxy. $R_1$ is β-hydroxy.

In another aspect, the present invention provides compounds where $R_1$ is halogen. $R_1$ is fluorine. $R_1$ is α-fluorine. $R_1$ is β-fluorine. The stereochemistry of $R_1$ in the α- and β-configurations is shown below:

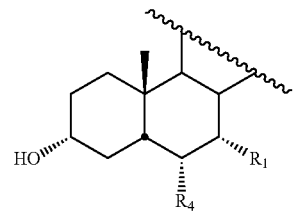

$R_1$ alpha (α-) configuration

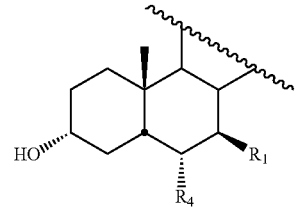

$R_1$ beta (β-) configuration

In another aspect, the present invention provides compounds where $R_2$ is α-hydroxy. $R_2$ is hydrogen. $R_1$ is β-hydroxy and $R_2$ is α-hydroxy. $R_1$ is β-hydroxy and $R_2$ is H. $R_1$ is α-hydroxy and $R_2$ is H.

In another aspect, the present invention provides compounds where at least one of $R_1$ or $R_2$ is hydroxy. In another aspect, at least one of $R_1$ or $R_2$ is hydrogen. $R_1$ and $R_2$ are the same. $R_1$ and $R_2$ are each α-hydroxy. $R_1$ and $R_2$ are each hydrogen.

In another aspect, the present invention provides compounds where $R_3$ is hydrogen, hydroxyl, $NH(CH_2)_mSO_3H$, or $NH(CH_2)_nCO_2H$. $R_3$ is hydroxyl. $R_3$ is not hydroxyl. $R_3$ is NH(CH$_2$)$_m$SO$_3$H. In another aspect, R$_3$ is NH(CH$_2$)$_m$SO$_3$H and m is 2. R$_3$ is NH(CH$_2$)$_n$CO$_2$H. In another aspect, R$_3$ is NH(CH$_2$)$_n$CO$_2$H and n is 1.

In another aspect, R$_4$ is hydrogen or alkyl. R$_4$ is hydrogen. R$_4$ is lower alkyl. R$_4$ is lower alkyl and the lower alkyl group is in the alpha configuration. R$_4$ in the alpha configuration means that R$_4$ has the stereochemistry shown in the structure below.

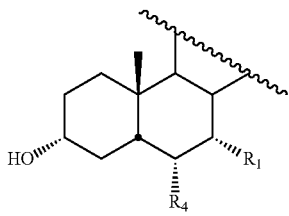

R$_4$ alpha (α-) configuration

In another aspect, R$_4$ is halogen. R$_4$ is fluorine. R$_4$ is halogen and the halogen is in the alpha configuration. R$_4$ is α-fluorine.

In another aspect, R$_4$ is methyl or ethyl. R$_4$ is methyl. R$_4$ is ethyl. R$_4$ is α-methyl. R$_4$ is α-ethyl. R$_3$ and R$_4$ are the same. R$_3$ and R$_4$ are different. R$_3$ and R$_4$ are each hydrogen. R$_3$ is NH(CH$_2$)$_m$SO$_3$H and R$_4$ is hydrogen. R$_3$ is hydroxyl and R$_4$ is hydrogen. In another aspect, R$_3$ is NH(CH$_2$)$_m$SO$_3$H, R$_4$ is hydrogen and m is 2. R$_3$ is NH(CH$_2$)$_n$CO$_2$H and R$_4$ is hydrogen. In another aspect, R$_3$ is NH(CH$_2$)$_n$CO$_2$H, R$_4$ is hydrogen and n is 1.

In another aspect, R$_3$ is OH and R$_4$ is alkyl. R$_3$ is OH and R$_4$ is lower alkyl. Lower alkyl is in the alpha configuration. R$_3$ is OH and R$_4$ is methyl. R$_3$ is OH and R$_4$ is ethyl. R$_3$ is OH and R$_4$ is α-methyl. R$_3$ is OH and R$_4$ is α-ethyl.

In another aspect, R$_5$ is unsubstituted or substituted alkyl. R$_5$ is unsubstituted or substituted lower alkyl. R$_5$ is in the S-configuration. R$_5$ is in the R-configuration. R$_5$ is methyl or ethyl. R$_5$ is S-methyl. R-methyl. R$_5$ is S-ethyl. R-ethyl. R$_5$ is alkyl substituted with phenyl. R$_5$ is lower alkyl substituted with phenyl. R$_5$ is benzyl. R$_5$ is S-benzyl. R$_5$ is R-benzyl.

In another aspect, R$_5$ is aryl. R$_5$ is phenyl.

In another aspect, R$_4$ and R$_5$ are each unsubstituted alkyl. R$_4$ and R$_5$ are each lower unsubstituted alkyl. R$_4$ and R$_5$ are each lower unsubstituted alkyl and R$_5$ is in the S-configuration. R$_4$ and R$_5$ are each lower unsubstituted alkyl and R$_4$ is in the alpha configuration. In another aspect, R$_4$ is not hydrogen.

In another aspect, R$_4$ and R$_5$ are each lower unsubstituted alkyl and R$_1$ is α-hydroxy. R$_4$ and R$_5$ are each lower unsubstituted alkyl and R$_2$ is hydrogen. R$_4$ and R$_5$ are each lower unsubstituted alkyl, R$_1$ is α-hydroxy, and R$_2$ is hydrogen.

In another aspect, R$_5$ and R$_6$ taken together with the carbons to which they are attached form a ring size of 3, 4, 5, or 6 atoms. R$_5$ and R$_6$ taken together with the carbons to which they are attached form a 3-membered ring. The 3-membered ring has the following stereochemistry:

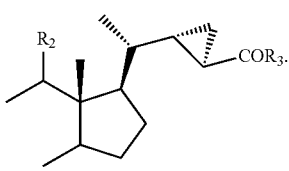

The 3-membered ring has the following stereochemistry:

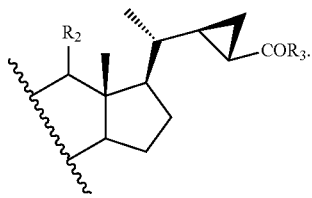

In another aspect, R$_1$, R$_2$, R$_3$, and R$_4$ are hydrogen. R$_2$, R$_3$, and R$_4$ are hydrogen. R$_2$ and R$_3$ are hydrogen. In another aspect, R$_1$, R$_2$, and R$_4$ are hydrogen and R$_3$ is OH. R$_2$ and R$_4$ are hydrogen and R$_3$ is OH. R$_2$ is hydrogen and R$_3$ is OH.

In another aspect, at least one of R$_1$, R$_2$, R$_3$, or R$_4$ is hydrogen.

In another aspect, at least two of R$_1$, R$_2$, R$_3$, or R$_4$ are hydrogen.

In another aspect, at least three of R$_1$, R$_2$, R$_3$, or R$_4$ are hydrogen.

In another aspect, R$_1$, R$_2$, R$_3$, and R$_4$ are hydrogen.

In another aspect, at least one of R$_1$, R$_2$, or R$_4$ is hydrogen and R$_3$ is OH.

In another aspect, at least two of R$_1$, R$_2$, or R$_4$ are hydrogen and R$_3$ is OH.

In another aspect, all of R$_1$, R$_2$, and R$_4$ are hydrogen and R$_3$ is OH.

In another aspect, the present invention does not include when R$_5$ is methyl, R$_4$ is hydrogen, and R$_2$ is H or OH.

In another aspect of the present invention, the compound is selected from Compounds Ia, Ib, Ic, Ig, Ih, Ii, Io, Ip, Iq, Ia1, Ib1, Ic1, Ig1, Ih1, Ii1, Il1, Im1, In1, Io1, Ip1, Iq1, Ia2, Ib2, Ic2, Id2, Ie2, If2, Ig2, Ih2, Ii2, Il2, Im2, In2, Io2, Ip2, Iq2, Ia3, Ib3, Ic3, Id3, Ie3, If3, Ig3, Ih3, Ii3, Il3, Im3, In3, Ia4, Ib4, Ic4, Id4, Ie4, If4, Ig4, Ih4, Ii4, Il4, Im4, In4, Ia5, Ib5, Ic5, Id5, Ie5, If5, Ig5, Ih5, Ii5, Il5, Im5 and In5.

In another aspect of the present invention, the compound is not selected from Compounds Id, Ie, If, Id1, Il, Im, and In. In another aspect, the compound is not selected from Ie1 and If1.

In another aspect of the present invention, the compounds are modulate the activity of TGR5 receptor. The present invention includes compounds that are TGR5 receptor agonists. In one aspect, the present invention includes compounds that are highly selective for the TGR5 receptor over the FXR receptor.

Another aspect of the present invention includes a composition or medicament comprising a compound of formula I:

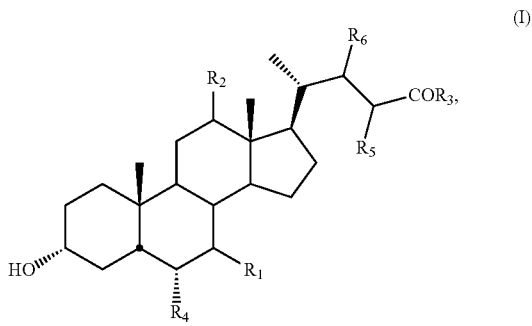

(I)

or a pharmaceutically acceptable salt, solvate, hydrate, or prodrug thereof, and at least one pharmaceutically acceptable excipient wherein $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, unsubstituted or substituted alkyl, or halogen; $R_5$ is unsubstituted or substituted lower alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5; and n is an integer 0, 1, 2, 3, 4, or 5. In another aspect, the present invention includes a composition or medicament comprising a compound of formula I with proviso that when $R_5$ is methyl, $R_1$ is hydroxyl, and $R_3$ is hydroxy or $NHCH_2CH_2SO_3H$, then $R_4$ is not hydrogen.

Another aspect of the invention includes a method of treating and/or preventing disease in a subject, comprising administering an effective amount of a compound of formula I to a subject in need thereof:

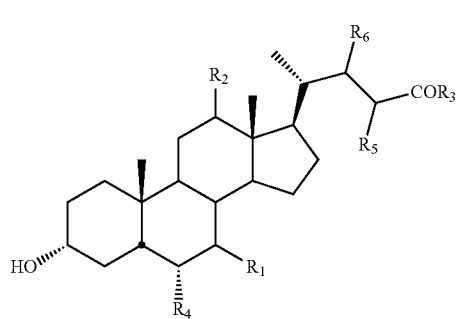

(I)

or a pharmaceutically acceptable salt, solvate, hydrate, or prodrug thereof, wherein: $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, unsubstituted or substituted alkyl, or halogen; $R_5$ is unsubstituted or substituted alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5; and n is an integer 0, 1, 2, 3, 4, or 5. The present invention includes a method for treatment and/or prevention of a disease or condition that involves modulation of the TGR5 receptor.

The present invention includes a method comprising administering a compound of formula I. The present invention includes a method comprising administering a therapeutically effective amount of a compound of formula I. The present invention includes a method comprising administering a prophylactically effective amount of a compound of formula I.

In one aspect of the present invention, the compound is a regulator of a physiological function in which TGR5 is involved, or an agent for the prophylaxis or treatment of pathology or disease in which TGR5 is involved. In another aspect, the compound is a cytokine production suppressor. In another aspect, the compound is a GLP-1 secretion promoter or an insulin secretagogue. In another aspect, the compound is an anorectic agent, a pancreatic regenerator, a pancreatic β cell differentiation promoter, a pancreatic β cell growth promoter or an insulin sensitizer. In another aspect, the compound is an agent for the prophylaxis or treatment of cardiac failure, cardiac infarction, acute kidney failure, angina pectoris, arrhythmia, bronchial asthma, chronic obstructive pulmonary disease, arteriosclerosis, rheumatoid arthritis, diabetes, obesity, insulin hyposecretion, pancreatic fatigue, gastric ulcer, ulcerative colitis, allergy, osteoarthritis, erythematosus, excessive immune reaction after transplantation or infectious disease, or an immunosuppressant.

The present invention includes a method of treatment of a subject affected by a disease wherein the TGR5 receptor is involved, which method includes administration to a subject a compound of formula I.

In another aspect, the invention includes a method for treatment or prevention of a metabolic disease by administering a compound of the invention. In one aspect, the metabolic disease is obesity. In another aspect, the metabolic disease is insulin sensitivity. In another aspect, the metabolic disease is diabetes. In another aspect, the metabolic disease is insulin hyposecretion. In another aspect, the metabolic disease is pancreatic fatigue.

The present invention includes a method for treatment and/or prevention of an inflammatory disease by administering a compound of the invention. In one aspect, the inflammatory disease is rheumatoid arthritis. In another aspect, the inflammatory disease is allergy.

The present invention includes the subject is human.

The present invention includes use of the compounds of the invention for known traditional uses of the bile acids. Traditional uses of the bile acids include treatment of cholelithiasis, bile desaturation, cholesterol metabolism, and use as an antioxidant, radical scavenger, anticholestatic, enduretic, anti-dyslipemic, and hepatocycle protector.

In another aspect, the method comprises administering a compound of formula I where if $R_5$ is methyl; $R_1$ is hydroxy; $R_3$ is hydroxyl or $NHCH_2CH_2SO_3H$, then $R_4$ is not hydrogen.

In another aspect, the method includes administering a compound selected from Compounds Ia, Ib, Ic, Id, Ie, If, Ig, Ih, Ii, Il, Im, In, Io, Ip, Iq, Ia1, Ib1, Ic1, Id1, Ie1, If1, Ig1, Ih1, Ii1, Il1, Im1, In1, Io1, Ip1, Iq1, Ia2, Ib2, Ic2, Id2, Ie2, If2, Ig2, Ih2, Ii2, Il2, Im2, In2, Io2, Ip2, Iq2, Ia3, Ib3, Ic3, Id3, Ie3, If3, Ig3, Ih3, Ii3, Il3, Im3, In3, Ia4, Ib4, Ic4, Id4, Ie4, If4, Ig4, Ih4, Ii4, Il4, Im4, In4, Ia5, Ib5, Ic5, Id5, Ie5, If5, Ig5, Ih5, Ii5, Il5, Im5 and In5.

In another aspect, the method includes administering a compound selected from Compounds Ia, Ib, Ic, Ig, Ih, Ii, Io, Ip, Iq, Ia1, Ib1, Ic1, Ig1, Ih1, Ii1, Il1, Im1, In1, Io1, Ip1, Iq1, Ia2, Ib2, Ic2, Id2, Ie2, If2, Ig2, Ih2, Ii2, Il2, Im2, In2, Io2, Ip2, Iq2, Ia3, Ib3, Ic3, Id3, Ie3, If3, Ig3, Ih3, Ii3, Il3, Im3, In3, Ia4, Ib4, Ic4, Id4, Ie4, If4, Ig4, Ih4, Ii4, Il4, Im4, In4, Ia5, Ib5, Ic5, Id5, Ie5, If5, Ig5, Ih5, Ii5, Il5, Im5 and In5.

In one aspect, the method of the present invention does not include administering a compound selected from Compounds Id, Ie, If, Id1, Il, Im, and In. In another aspect, the method of the present invention does not include administering Ie1 and If1.

Another aspect of the present invention is the use of a compound of formula I:

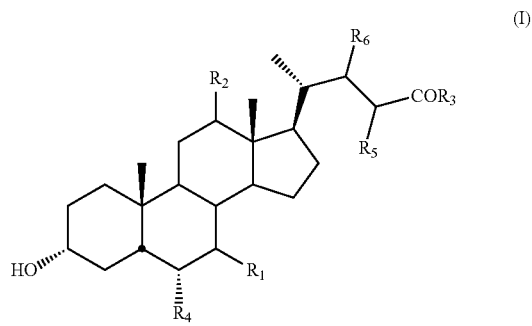

(I)

or a pharmaceutically acceptable salt, solvate, hydrate, or prodrug thereof, and at least one pharmaceutically acceptable excipient wherein $R_1$ is hydrogen, hydroxy, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, alkyl, or halogen; $R_5$ is unsubstituted or substituted lower alkyl, or aryl; $R_6$ is hydrogen or $R_5$ and $R_6$ taken together with the carbons to which they are attached form a ring of size 3, 4, 5, or 6 atoms; m is an integer 0, 1, 2, 3, 4, or 5; and n is an integer 0, 1, 2, 3, 4, or 5 for the preparation of a medicament for the treatment and/or prevention of disease wherein a modulation of TGR5 is desired. In another aspect, the present invention includes a use for the preparation of a medicament for the treatment and/or prevention of disease wherein a modulation of TGR5 is desired comprising a compound of formula I with proviso that when $R_5$ is methyl, $R_1$ is hydroxyl, and $R_3$ is hydroxy or $NHCH_2CH_2SO_3H$, then $R_4$ is not hydrogen.

The present invention also provides radiolabeled compounds of formula I. Radiolabeled compounds of formula I can be prepared using conventional techniques. For example, radiolabeled compounds of formula I can be prepared by reacting the compound of formula I with tritium gas in the presence of an appropriate catalyst to produce radiolabeled compounds of formula I. In one embodiment, the compounds of formula I are tritiated.

Another aspect of the invention includes compounds of Formula IA:

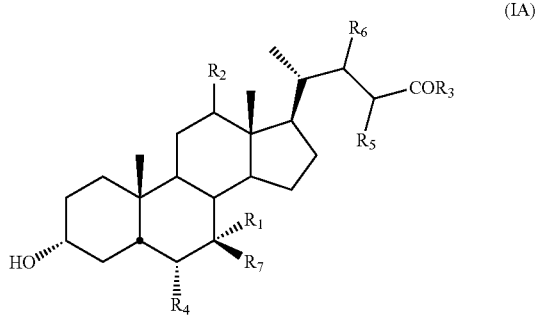

(IA)

or a pharmaceutically acceptable salt, solvate, hydrate, or prodrug thereof, wherein: $R_1$ is hydrogen, hydroxy, substituted or unsubstituted alkyl, or halogen; $R_2$ is hydrogen or α-hydroxy; $R_3$ is hydroxy, hydrogen, $NH(CH_2)_mSO_3H$, or $NH(CH_2)_nCO_2H$; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; m is an integer 0, 1, 2, 3, 4, or 5; and n is an integer 0, 1, 2, 3, 4, or 5. In one aspect, when $R_5$ is methyl, $R_1$ is hydroxyl, and $R_3$ is hydroxy or $NHCH_2CH_2SO_3H$, then $R_4$ is not hydrogen.

In one aspect, $R_1$ is hydrogen or hydroxy. $R_1$ is hydroxy. $R_1$ is hydrogen. $R_1$ is hydroxy and $R_2$ is α-hydroxy. $R_1$ is hydroxy and $R_2$ is H. $R_1$ is hydroxy and $R_2$ is H. At least one of $R_1$ or $R_2$ is hydroxy. At least one of $R_1$ or $R_2$ is hydrogen. $R_1$ and $R_2$ are the same. $R_1$ is hydroxyl and $R_2$ is α-hydroxy. $R_1$ and $R_2$ are each hydrogen.

In one aspect, $R_3$ is hydrogen, hydroxy, $NH(CH_2)_mSO_3H$, or $NH(CH_2)_nCO_2H$. $R_3$ is hydroxy. $R_3$ is not hydroxy. $R_3$ is $NH(CH_2)_mSO_3H$. $R_3$ is $NH(CH_2)_mSO_3H$ and m is 2. $R_3$ is $NH(CH_2)_nCO_2H$. $R_3$ is $NH(CH_2)_nCO_2H$ and n is 1.

In another aspect, $R_4$ is hydrogen or unsubstituted alkyl. $R_4$ is hydrogen. $R_4$ is unsubstituted alkyl. $R_4$ is unsubstituted alkyl. $R_4$ is methyl or ethyl. $R_4$ is methyl. $R_4$ is ethyl. $R_3$ and $R_4$ are the same. $R_3$ and $R_4$ are different. $R_3$ and $R_4$ are each hydrogen. $R_3$ is OH and $R_4$ is hydrogen.

In another aspect, $R_3$ is $NH(CH_2)_mSO_3H$ and $R_4$ is hydrogen. $R_3$ is $NH(CH_2)_mSO_3H$, $R_4$ is hydrogen, and m is 2. $R_3$ is $NH(CH_2)_nCO_2H$ and $R_4$ is hydrogen. $R_3$ is $NH(CH_2)_nCO_2H$, $R_4$ is hydrogen, and n is 1. $R_3$ is OH and $R_4$ is unsubstituted alkyl. $R_3$ is OH and $R_4$ is unsubstituted alkyl. $R_3$ is OH and $R_4$ is methyl. $R_3$ is OH and $R_4$ is ethyl. $R_3$ is OH and $R_4$ is methyl.

In one aspect, $R_5$ is unsubstituted or substituted alkyl. $R_5$ is in the S-configuration. $R_5$ is in the R-configuration. $R_5$ is methyl or ethyl. $R_5$ is S-methyl. $R_5$ is R-methyl. $R_5$ is S-ethyl. $R_5$ is R-ethyl. $R_5$ is substituted with phenyl. $R_5$ is benzyl. $R_5$ is S-benzyl. $R_5$ is R-benzyl. In another aspect, $R_5$ is aryl. For example, $R_5$ is phenyl.

$R_4$ and $R_5$ are each unsubstituted alkyl. $R_4$ and $R_5$ are each unsubstituted alkyl, further wherein $R_5$ is in the S-configuration. $R_4$ and $R_5$ are each unsubstituted alkyl. $R_4$ and $R_5$ are each unsubstituted alkyl and $R_1$ is hydroxy. $R_4$ and $R_5$ are each unsubstituted alkyl and $R_2$ is hydrogen. $R_4$ and $R_5$ are each unsubstituted alkyl, $R_1$ is hydroxy, and $R_2$ is hydrogen.

In one aspect, $R_1$, $R_2$, $R_3$, and $R_4$ are hydrogen. $R_2$, $R_3$, and $R_4$ are hydrogen. $R_2$ and $R_3$ are hydrogen. At least one of $R_1$, $R_2$, $R_3$, or $R_4$ is hydrogen. At least two of $R_1$, $R_2$, $R_3$, or $R_4$ is hydrogen. At least three of $R_1$, $R_2$, $R_3$, or $R_4$ is hydrogen. $R_1$, $R_2$, $R_3$, and $R_4$ are hydrogen.

In one aspect, $R_1$, $R_2$, and $R_4$ are hydrogen and $R_3$ is OH. $R_2$ and $R_4$ are hydrogen and $R_3$ is OH. $R_2$ is hydrogen and $R_3$ is OH. At least one of $R_1$, $R_2$, or $R_4$ is hydrogen and $R_3$ is OH. At least two of $R_1$, $R_2$, or $R_4$ is hydrogen and $R_3$ is OH. At least three of $R_1$, $R_2$, or $R_4$ is hydrogen and $R_3$ is OH. All of $R_1$, $R_2$, and $R_4$ are hydrogen and $R_3$ is OH.

In another aspect, at least one of $R_1$ or $R_7$ is unsubstituted alkyl. At least one of $R_1$ or $R_7$ is methyl. At least one of $R_1$ or $R_7$ is ethyl. At least one of $R_1$ or $R_7$ is propyl. Both $R_1$ and $R_7$ are unsubstituted alkyl. Both $R_1$ and $R_7$ are methyl. Both $R_1$ and $R_7$ are ethyl. $R_1$ and $R_7$ are the same. $R_1$ and $R_7$ are different. $R_7$ is hydrogen. $R_7$ is hydroxy. One of $R_1$ or $R_7$ is unsubstituted alkyl and the remaining $R_1$ or $R_7$ is hydrogen. One of $R_1$ or $R_7$ is unsubstituted alkyl and the remaining $R_1$ or $R_7$ is hydroxy. At least one of $R_1$ or $R_7$ is unsubstituted alkyl and $R_5$ is unsubstituted or substituted alkyl. At least one of $R_1$ or $R_7$ is methyl and $R_5$ is methyl.

Both $R_1$ and $R_5$ are unsubstituted alkyl and $R_7$ is hydroxy. Both $R_7$ and $R_5$ are unsubstituted alkyl and $R_1$ is hydroxy. $R_1$ or $R_7$ is unsubstituted alkyl and $R_5$ is unsubstituted or substituted alkyl further wherein $R_5$ is in the S-configuration. $R_1$ or $R_7$ is unsubstituted alkyl and $R_5$ is unsubstituted or substituted alkyl, further wherein $R_5$ is in the R-configuration.

In another aspect, $R_1$ is hydroxy and $R_7$ is methyl. $R_1$ is methyl and $R_7$ is hydroxy. $R_6$ is unsubstituted alkyl. $R_6$ is methyl. $R_6$ is ethyl. $R_2$ and $R_6$ are each hydrogen. $R_2$ and $R_6$ are hydrogen and $R_5$ is unsubstituted alkyl. $R_2$ and $R_6$ are hydrogen, $R_5$ is unsubstituted alkyl, and at least one of $R_1$ or $R_7$ is unsubstituted alkyl.

In one aspect, the compound is selected from Compounds Ia6, Ib6, Ic6, Ig6, Ih6, Ii6, Io6, Ip6, Iq6, Ia7, Ib7, Ic7, Ig7, Ih7, Ii7, Il7, Im7, In7, Io7, Ip7, Iq7, Ia8, Ib8, Ic8, Id8, Ie8, If8, Ig8, Ih8, Ii8, Il8, Im8, In8, Io8, Ip8, Iq8, Ia9, Ib9, Ic9, Id9, Ie9, If9, Ig9, Ih9, Ii9, Il9, Im9, In9, Ia10, Ib10, Ic10, Id10, Ie10, If10, Ig10, Ih10, Ii10, Il10, Im10, In10, Ia11, Ib11, Ic11, Id11, Ie11, If11, Ig11, Ih11, Ii11, Il11, Im11 and In11.

In another aspect of the present invention, when $R_2$, $R_4$, and $R_6$ are each hydrogen, $R_3$ is hydroxyl, and one of $R_1$ and $R_7$ is hydrogen or hydroxyl, then the other $R_1$ or $R_7$ is not methyl.

In another aspect, when $R_2$ is α-OH; $R_3$ is hydroxyl; $R_4$ and $R_6$ are each hydrogen; and one of $R_1$ and $R_7$ is hydrogen or hydroxyl, then the other $R_1$ or $R_7$ is not methyl. In another aspect, the present invention does not include the following compounds: 3α,7α-dihydroxy-7β-methyl-5β-cholanoic acid, 3α,7β-dihydroxy-7α-methyl-5β-cholanoic acid, 3α-hydroxy-7ε-methyl-5β-cholanoic acid, 3α,7β,12α-trihydroxy-7α-methyl-5β-cholan-24-oic acid; 3α,7α,12α-trihydroxy-7β-methyl-5β-cholan-24-oic acid; and 3α,12α-dihydroxy-7ε-methyl-5β-cholan-24-oic acid.

In another aspect of the present invention, when $R_3$ is hydroxyl and one of $R_1$ and $R_7$ is methyl and the other $R_1$ and $R_7$ is hydrogen or hydroxyl, then $R_2$, $R_4$ and $R_6$ are not all hydrogen. In another aspect, when $R_2$ is α-OH, $R_3$ is hydroxyl, and one of $R_1$ and $R_7$ is methyl and the other $R_1$ and $R_7$ is hydrogen or hydroxyl, then $R_4$ and $R_6$ are not all hydrogen.

Another aspect of the invention includes a composition or medicament comprising a compound of formula IA:

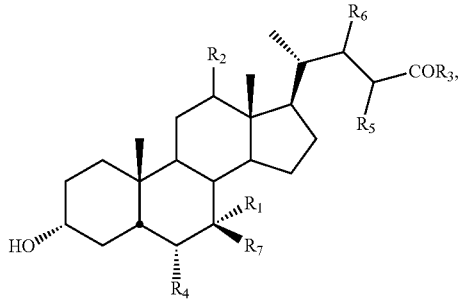

(IA)

or a pharmaceutically acceptable salt, solvate, hydrate, or prodrug thereof, and at least one pharmaceutically acceptable excipient wherein: $R_1$ is hydrogen, hydroxy, substituted or unsubstituted alkyl or halogen; $R_2$ is hydrogen or α-hydroxy; $R_3$ is hydroxy, $NH(CH_2)_mSO_3H$, or $NH(CH_2)_nCO_2H$; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; and m is an integer 0, 1, 2, 3, 4, or 5; and n is an integer 0, 1, 2, 3, 4, or 5.

In one aspect of the invention, when $R_5$ is methyl, $R_1$ is hydroxyl, and $R_3$ is hydroxyl or $NHCH_2CH_2SO_3H$, then $R_4$ is not hydrogen.

Another aspect of the invention includes a method of treating and/or preventing disease in a subject, comprising administering a compound of formula IA to a subject in need thereof:

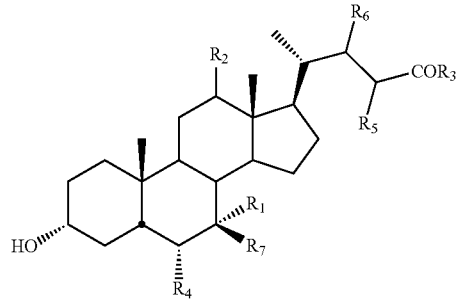

(IA)

or a pharmaceutically acceptable salt, solvate, hydrate, or prodrug thereof, wherein: $R_1$ is hydrogen, hydroxy, substituted or unsubstituted alkyl, or halogen; $R_2$ is hydrogen or α-hydroxy; $R_3$ is hydroxy, $NH(CH_2)_mSO_3H$, or $NH(CH_2)_nCO_2H$; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; m is an integer 0, 1, 2, 3, 4, or 5; and n is an integer 0, 1, 2, 3, 4, or 5. In one aspect, treatment and/or prevention of the disease involves modulation of TGR5 receptor in a subject. The disease is obesity. The disease is insulin sensitivity. The disease is inflammation. The subject is human.

In one aspect, when $R_5$ is methyl; $R_1$ is hydroxy; $R_3$ is hydrogen or $NHCH_2CH_2SO_3H$, then $R_4$ is not hydrogen. In another aspect, the method relates administering a compound selected from Compounds Ia6, Ib6, Ic6, Id6, Ie6, If6, Ig6, Ih6, Ii6, Il6, Im6, In6, Io6, Ip6, Iq6, Ia7, Ib7, Ic7, Id7, Ie7, If7, Ig7, Ih7, Ii7, Il7, Im7, In7, Io7, Ip7, Iq7, Ia8, Ib8, Ic8, Id8, Ie8, If8, Ig8, Ih8, Ii8, Il8, Im8, In8, Io8, Ip8, Ig8, Ia9, Ib9, Ic9, Id9, Ie9, If9, Ig9, Ih9, Ii9, Il9, Im9, In9, Ia10, Ib10, Ic10, Id10, Ie10, If10, Ig10, Ih10, Ii10, Il10, Im10, In10, Ia11, Ib11, Ic11, Id11, Ie11, If11, Ig11, Ih11, Ii11, Il11, Im11 and In11.

In another aspect, the method relates to administering a compound is selected from Compounds Ia6, Ib6, Ic6, Ig6, Ih6, Ii6, Io6, Ip6, Iq6, Ia7, Ib7, Ic7, Ig7, Ih7, Ii7, Il7, Im7, In7, Io7, Ip7, Iq7, Ia8, Ib8, Ic8, Id8, Ie8, If8, Ig8, Ih8, Ii8, Il8, Im8, In8, Io8, Ip8, Iq8, Ia9, Ib9, Ic9, Id9, Ie9, If9, Ig9, Ih9, Ii9, Il9, Im9, In9, Ia10, Ib10, Ic10, Id10, Ie10, If10, Ig10, Ih10, Ii10, Il10, Im10, In10, Ia11, Ib11, Ic11, Id11, Ie11, If11, Ig11, Ih11, Ii11, Il11, Im11 and In11.

In another aspect, the method relates to administering a compound of formula IA with the proviso that when $R_5$ is methyl, $R_1$ is hydroxyl, and $R_3$ is hydroxyl or $NHCH_2CH_2SO_3H$, then $R_4$ is not hydrogen.

The present invention includes a method of treating and/or preventing disease in a subject, comprising administering a compound of formula IA to a subject in need thereof. The disease is selected from cholestasis or bile desaturation. The present invention relates to the use of compound of formula IA in the preparation or manufacture of a medicament for treating and/or preventing disease involving the modulation of the TGR5 receptor in a subject, comprising administering said compound to a subject in need thereof.

The present invention also provides radiolabeled compounds of formula IA. Radiolabeled compounds of formula IA can be prepared using conventional techniques. For example, radiolabeled compounds of formula IA can be prepared by reacting the compound of formula IA with tritium gas in the presence of an appropriate catalyst to produce radiolabeled compounds of formula IA. In one embodiment, the compounds of formula IA are tritiated.

Another aspect of the present invention includes a compound of Formula II:

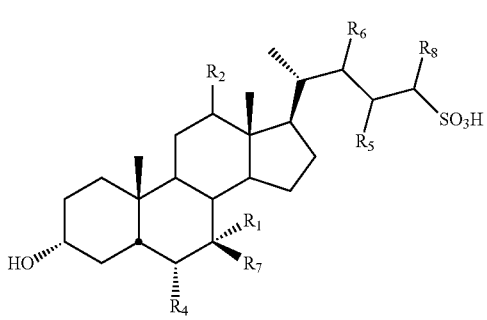

or a pharmaceutically acceptable salt, solvate, hydrate, or prodrug thereof, wherein: $R_1$ is hydrogen, hydroxy, substituted or unsubstituted alkyl, or halogen; $R_2$ is hydrogen or α-hydroxy; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; and $R_8$ is hydrogen, substituted or unsubstituted alkyl. In one aspect, when $R_5$ is methyl and $R_1$ is hydroxyl, then $R_4$ is not hydrogen.

In one aspect, $R_1$ is hydrogen or hydroxy. $R_1$ is hydroxy. $R_1$ is hydrogen. $R_1$ is β-hydroxy. $R_2$ is α-hydroxy. $R_1$ is hydroxy and $R_2$ is α-hydroxy. $R_1$ is hydroxy and $R_2$ is H. At least one of $R_1$ or $R_2$ is hydroxy. At least one of $R_1$ or $R_2$ is hydrogen. $R_1$ and $R_2$ are the same. $R_1$ is hydroxyl and $R_2$ is α-hydroxy. $R_1$ and $R_2$ are each hydrogen.

In another aspect, $R_4$ is hydrogen or unsubstituted alkyl. $R_4$ is hydrogen. $R_4$ is unsubstituted alkyl. $R_4$ is unsubstituted alkyl. $R_4$ is methyl or ethyl. $R_4$ is methyl. $R_4$ is ethyl.

In one aspect, $R_5$ is unsubstituted or substituted alkyl. $R_5$ is in the S-configuration. $R_5$ is in the R-configuration. $R_5$ is methyl or ethyl. $R_5$ is S-methyl. $R_5$ is R-methyl. $R_5$ is S-ethyl. $R_5$ is R-ethyl. $R_5$ is substituted with phenyl. $R_5$ is benzyl. $R_5$ is S-benzyl. $R_5$ is R-benzyl. $R_5$ is aryl. $R_5$ is phenyl. $R_4$ and $R_5$ are each unsubstituted alkyl. $R_4$ and $R_5$ are each unsubstituted alkyl, further wherein $R_5$ is in the S-configuration. $R_4$ and $R_5$ are each unsubstituted alkyl and $R_1$ is hydroxy. $R_4$ and $R_5$ are each unsubstituted alkyl and $R_2$ is hydrogen. $R_4$ and $R_5$ are each unsubstituted alkyl, $R_1$ is hydroxy, and $R_2$ is hydrogen.

In one aspect, $R_1$, $R_2$, and $R_4$ are hydrogen. $R_2$ and $R_4$ are hydrogen. $R_2$ is hydrogen. At least one of $R_1$, $R_2$, or $R_4$ is hydrogen. At least two of $R_1$, $R_2$, or $R_4$ is hydrogen. $R_1$, $R_2$, and $R_4$ are hydrogen.

In one aspect, $R_1$ or $R_7$ is unsubstituted alkyl. $R_1$ or $R_7$ is methyl. $R_1$ or $R_7$ is ethyl. $R_1$ or $R_7$ is propyl. Both $R_1$ and $R_7$ are unsubstituted alkyl. $R_7$ is hydrogen. $R_7$ is hydroxy. One of $R_1$ or $R_7$ is unsubstituted alkyl and the remaining $R_1$ or $R_7$ is hydrogen. One of $R_1$ or $R_7$ is unsubstituted alkyl and the remaining $R_1$ or $R_7$ is hydroxy. At least one of $R_1$ or $R_7$ is unsubstituted alkyl and $R_5$ is unsubstituted or substituted alkyl. At least one of $R_1$ or $R_7$ is methyl and $R_5$ is methyl. $R_7$ is hydroxy and both $R_1$ and $R_5$ are unsubstituted alkyl. $R_1$ is hydroxy and both $R_7$ and $R_5$ are unsubstituted alkyl. At least one of $R_1$ or $R_7$ is unsubstituted alkyl and $R_5$ is unsubstituted or substituted alkyl, further wherein $R_5$ is in the S-configuration. At least one of $R_1$ or $R_7$ is unsubstituted alkyl and $R_5$ is unsubstituted or substituted alkyl, further wherein $R_5$ is in the R-configuration. $R_7$ is hydroxy and both $R_1$ and $R_5$ are unsubstituted alkyl, further wherein $R_5$ is in the S-configuration. $R_7$ is hydroxy and both $R_1$ and $R_5$ are unsubstituted alkyl, further wherein $R_5$ is in the R-configuration. $R_1$ is hydroxy and both $R_7$ and $R_5$ are unsubstituted alkyl, further wherein $R_5$ is in the S-configuration. $R_1$ is hydroxy and both $R_7$ and $R_5$ are unsubstituted alkyl, further wherein $R_5$ is in the R-configuration. $R_1$ is hydroxy and $R_7$ is methyl. $R_1$ is methyl and $R_7$ is hydroxy.

In another aspect, $R_6$ is unsubstituted alkyl. $R_6$ is methyl. $R_6$ is ethyl. $R_8$ is hydrogen.

$R_8$ is unsubstituted alkyl. $R_8$ is methyl. $R_8$ is ethyl. $R_2$ is α-hydroxy and $R_8$ is unsubstituted alkyl.

In another aspect of the invention, the compound is selected from Compounds Ia12, Ib12, Ic12, Ig12, Ih12, Ii12, Io12, Ip12, Iq12, Ia13, Ib13, Ic13, Ig13, Ih13, Ii13, Il13, Im13, In13, Io13, Ip13, Iq13, Ia14, Ib14, Ic14, Id14, Ie14, If14, Ig14, Ih14, Il14, Il14, Im14, In14, Io14, Ip14, Iq14, Ia15, Ib15, Ic15, Id15, Ie15, If15, Ig15, Ih15, Ii15, Il15, Im15, In15, Ia16, Ib16, Ic16, Id16, Ie16, If16, Ig16, Ih16, Ii16, Il16, Im16, In16, Ia17, Ib17, Ic17, Id17, Ie17, If17, Ig17, Ih17, Ii17, Il17, Im17 and In17.

Another aspect of the invention includes a composition or medicament comprising a compound of formula II:

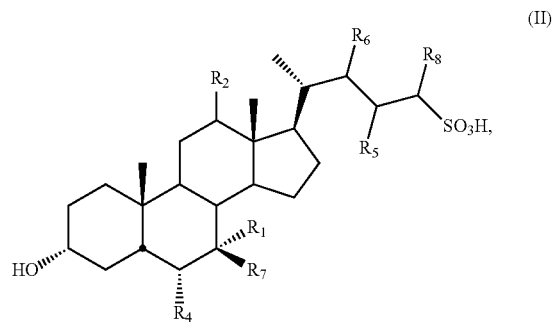

or a pharmaceutically acceptable salt, solvate, hydrate, or prodrug thereof, and at least one pharmaceutically acceptable excipient wherein: $R_1$ is hydrogen, hydroxy, substituted or unsubstituted alkyl or halogen; $R_2$ is hydrogen or α-hydroxy; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; and $R_8$ is hydrogen or substituted or unsubstituted alkyl. In one aspect, when $R_5$ is methyl, $R_1$ is hydroxyl, and $R_3$ is hydroxyl or $NHCH_2CH_2SO_3H$, then $R_4$ is not hydrogen.

In one aspect the invention includes a method of treating and/or preventing disease in a subject, comprising administering a compound of formula II to a subject in need thereof:

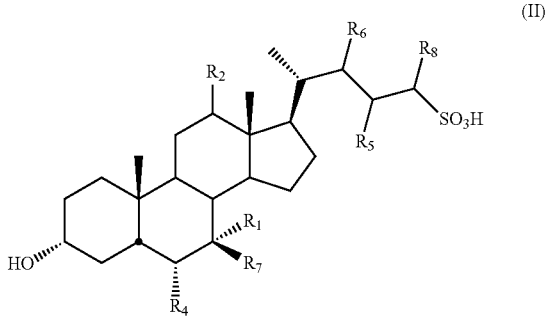
(II)

or a pharmaceutically acceptable salt, solvate, hydrate, or prodrug thereof, wherein:

$R_1$ is hydrogen, hydroxy, substituted or unsubstituted alkyl, or halogen; $R_2$ is hydrogen or α-hydroxy; $R_4$ is hydrogen, substituted or unsubstituted alkyl, or halogen; $R_5$ is unsubstituted or substituted alkyl, or aryl; $R_6$ is hydrogen, unsubstituted or substituted alkyl, or $R_5$ and $R_6$ taken together with the carbons to which they are attached form a ring of size 3, 4, 5, or 6 atoms; $R_7$ is hydrogen, substituted or unsubstituted alkyl, or hydroxy; and $R_8$ is hydrogen, substituted or unsubstituted alkyl.

The invention includes a method of treatment of a disease which involves modulation of the TGR5 receptor. The invention includes a method of prevention of a disease which involves modulation of the TGR5 receptor. The disease is obesity. The disease is insulin sensitivity. The disease is inflammation. The subject is human. In one aspect, when $R_5$ is methyl; $R_1$ is hydroxy; $R_3$ is hydroxyl or $NHCH_2CH_2SO_3H$, then $R_4$ is not hydrogen.

One aspect of the invention relates to a method of administering a compound is selected from Compounds Ia12, Ib12, Ic12, Id12, Ie12, If12, Ig12, Ih12, Ii12, Il12, Im12, In12, Io12, Ip12, Iq12, Ia13, Ib13, Ic13, Id13, Ie13, If13, Ig13, Ih13, Ii13, Il13, Im13, In13, Io13, Ip13, Iq13, Ia14, Ib14, Ic14, Id14, Ie14, If14, Ig14, Ih14, Ii14, Il14, Im14, In14, Io14, Ip14, Iq14, Ia15, Ib15, Ic15, Id15, Ie15, If15, Ig15, Ih15, Ii15, Il15, Im15, In15, Ia16, Ib16, Ic16, Id16, Ie16, If16, Ig16, Ih16, Ii16, Il16, Im16, In16, Ia17, Ib17, Ic17, Id17, Ie17, If17, Ig17, Ih17, Ii17, Il17, Im17 and In17.

Another aspect of the invention relates to a method of administering a compound selected from Compounds Ia12, Ib12, Ic12, Ig12, Ih12, Ii12, Io12, Ip12, Ig12, Ia13, Ib13, Ic13, Ig13, Ih13, Ii13, Il13, Im13, In13, Io13, Ip13, Iq13, Ia14, Ib14, Ic14, Id14, Ie14, If14, Ig14, Ih14, Ii14, Il14, Im14, In14, Io14, Ip14, Iq14, Ia15, Ib15, Ic15, Id15, Ie15, If15, Ig15, Ih15, Ii15, Il15, Im15, In15, Ia16, Ib16, Ic16, Id16, Ie16, If16, Ig16, Ih16, Ii16, Il16, Im16, In16, Ia17, Ib17, Ic17, Id17, Ie17, If17, Ig17, Ih17, Ii17, Il17, Im17 and In17.

Another aspect of the invention includes a method related to administering a compound of formula II with the proviso that when $R_5$ is methyl, and $R_1$ is hydroxyl, then $R_4$ is not hydrogen.

The present invention includes a method of treating disease in a subject, comprising administering a therapeutically effective amount of the compound of formula II to a subject in need thereof. The present invention includes a method of preventing disease in a subject, comprising administering a prophylatically effective amount of the compound of formula II to a subject in need thereof. The disease is selected from cholestasis or bile desaturation. The present invention relates to use of a compound of formula II in preparation of a medicament for treating and/or preventing a disease involving the modulation of the TGR5 receptor in a subject, comprising administering an effective amount i.e. a therapeutically effective or prophylatically effective amount of said compound to a subject in need thereof.

The present invention also provides radiolabeled compounds of formula II. Radiolabeled compounds of formula II can be prepared using conventional techniques. For example, radiolabeled compounds of formula II can be prepared by reacting the compound of formula II with tritium gas in the presence of an appropriate catalyst to produce radiolabeled compounds of formula II. In one embodiment, the compounds of formula II are tritiated.

Some representative compounds of the invention are shown below.

The following compounds Ia-In5 pertain to at least formula I:

Ia: $R_1$=α-OH, $R_2$=H, $R_3$=OH, $R_4$=H, $R_5$=(S,R)Me, $R_6$=H
Ib: $R_1$=α-OH, $R_2$=H, $R_3$=OH, $R_4$=H, $R_5$=(S)Me, $R_6$=H
Ic: $R_1$=α-OH, $R_2$=H, $R_3$=OH, $R_4$=H, $R_5$=(R)Me, $R_6$=H
Id: $R_1$=β-OH, $R_2$=H, $R_3$=OH, $R_4$=H, $R_5$=(S,R)Me, $R_6$=H
Ie: $R_1$=β-OH, $R_2$=H, $R_3$=OH, $R_4$=H, $R_5$=(S)Me, $R_6$=H
If: $R_1$=β-OH, $R_2$=H, $R_3$=OH, $R_4$=H, $R_5$=(R)Me, $R_6$=H
Ig: $R_1$=α-OH, $R_2$=α-OH, $R_3$=OH, $R_4$=H, $R_5$=(S,R)Me, $R_6$=H
Ih: $R_1$=α-OH, $R_2$=α-OH, $R_3$=OH, $R_4$=H, $R_5$=(S)Me, $R_6$=H
Ii: $R_1$=α-OH, $R_2$=α-OH, $R_3$=OH, $R_4$=H, $R_5$=(R)Me, $R_6$=H
Il: $R_1$=β-OH, $R_2$=α-OH, $R_3$=OH, $R_4$=H, $R_5$=(S,R)Me, $R_6$=H
Im: $R_1$=β-OH, $R_2$=α-OH, $R_3$=OH, $R_4$=H, $R_5$=(S)Me, $R_6$=H
In: $R_1$=β-OH, $R_2$=α-OH, $R_3$=OH, $R_4$=H, $R_5$=(R)Me, $R_6$=H
Io: $R_1$=H, $R_2$=H, $R_3$=OH, $R_4$=H, $R_5$=(S,R)Me, $R_6$=H
Ip: $R_1$=H, $R_2$=H, $R_3$=OH, $R_4$=H, $R_5$=(S)Me, $R_6$=H
Iq: $R_1$=H, $R_2$=H, $R_3$=OH, $R_4$=H, $R_5$=(R)Me, $R_6$=H
Ia1: $R_1$=α-OH, $R_2$=H, $R_3$=$NHCH_2CH_2SO_3H$, $R_4$=H, $R_5$=(S,R)Me, $R_6$=H
Ib1: $R_1$=α-OH, $R_2$=H, $R_3$=$NHCH_2CH_2SO_3H$, $R_4$=H, $R_5$=(S)Me, $R_6$=H
Ic1: $R_1$=α-OH, $R_2$=H, $R_3$=$NHCH_2CH_2SO_3H$, $R_4$=H, $R_5$=(R)Me, $R_6$=H
Id1: $R_1$=β-OH, $R_2$=H, $R_3$=$NHCH_2CH_2SO_3H$, $R_4$=H, $R_5$=(S,R)Me, $R_6$=H
Ie1: $R_1$=β-OH, $R_2$=H, $R_3$=$NHCH_2CH_2SO_3H$, $R_4$=H, $R_5$=(S)Me, $R_6$=H
If1: $R_1$=β-OH, $R_2$=H, $R_3$=$NHCH_2CH_2SO_3H$, $R_4$=H, $R_5$=(R)Me, $R_6$=H
Ig1: $R_1$=α-OH, $R_2$=α-OH, $R_3$=$NHCH_2CH_2SO_3H$, $R_4$=H, $R_5$=(S,R)Me, $R_6$=H
Ih1: $R_1$=α-OH, $R_2$=α-OH, $R_3$=$NHCH_2CH_2SO_3H$, $R_4$=H, $R_5$=(S)Me, $R_6$=H
Ii1: $R_1$=α-OH, $R_2$=α-OH, $R_3$=$NHCH_2CH_2SO_3H$, $R_4$=H, $R_5$=(R)Me, $R_6$=H
Il1: $R_1$=β-OH, $R_2$=α-OH, $R_3$=$NHCH_2CH_2SO_3H$, $R_4$=H, $R_5$=(S,R)Me, $R_6$=H
Im1: $R_1$=β-OH, $R_2$=α-OH, $R_3$=$NHCH_2CH_2SO_3H$, $R_4$=H, $R_5$=(S)Me, $R_6$=H
In1: $R_1$=β-OH, $R_2$=α-OH, $R_3$=$NHCH_2CH_2SO_3H$, $R_4$=H, $R_5$=(R)Me, $R_6$=H
Io1: $R_1$=H, $R_2$=H, $R_3$=$NHCH_2CH_2SO_3H$, $R_4$=H, $R_5$=(S,R)Me, $R_6$=H
Ip1: $R_1$=H, $R_2$=H, $R_3$=$NHCH_2CH_2SO_3H$, $R_4$=H, $R_5$=(S)Me, $R_6$=H
Iq1: $R_1$=H, $R_2$=H, $R_3$=$NHCH_2CH_2SO_3H$, $R_4$=H, $R_5$=(R)Me, $R_6$=H
Ia2: $R_1$=α-OH, $R_2$=H, $R_3$=$NHCH_2CO_2H$, $R_4$=H, $R_5$=(S,R)Me, $R_6$=H
Ib2: $R_1$=α-OH, $R_2$=H, $R_3$=$NHCH_2CO_2H$, $R_4$=H, $R_5$=(S)Me, $R_6$=H

Ic2: $R_1=\alpha$-OH, $R_2$=H, $R_3$=NHCH$_2$CO$_2$H, $R_4$=H, $R_5$=(R)Me, $R_6$=H
Id2: $R_1=\beta$-OH, $R_2$=H, $R_3$=NHCH$_2$CO$_2$H, $R_4$=H, $R_5$=(S,R)Me, $R_6$=H
Ie2: $R_1=\beta$-OH, $R_2$=H, $R_3$=NHCH$_2$CO$_2$H, $R_4$=H, $R_5$=(S)Me, $R_6$=H
If2: $R_1=\beta$-OH, $R_2$=H, $R_3$=NHCH$_2$CO$_2$H, $R_4$=H, $R_5$=(R)Me, $R_6$=H
Ig2: $R_1=\alpha$-OH, $R_2=\alpha$-OH, $R_3$=NHCH$_2$CO$_2$H, $R_4$=H, $R_5$=(S,R)Me, $R_6$=H
Ih2: $R_1=\alpha$-OH, $R_2=\alpha$-OH, $R_3$=NHCH$_2$CO$_2$H, $R_4$=H, $R_5$=(S)Me, $R_6$=H
Ii2: $R_1=\alpha$-OH, $R_2=\alpha$-OH, $R_3$=NHCH$_2$CO$_2$H, $R_4$=H, $R_5$=(R)Me, $R_6$=H
Il2: $R_1=\beta$-OH, $R_2=\alpha$-OH, $R_3$=NHCH$_2$CO$_2$H, $R_4$=H, $R_5$=(S,R)Me, $R_6$=H
Im2: $R_1=\beta$-OH, $R_2=\alpha$-OH, $R_3$=NHCH$_2$CO$_2$H, $R_4$=H, $R_5$=(S)Me, $R_6$=H
In2: $R_1=\beta$-OH, $R_2=\alpha$-OH, $R_3$=NHCH$_2$CO$_2$H, $R_4$=H, $R_5$=(R)Me, $R_6$=H
Io2: $R_1$=H, $R_2$=H, $R_3$=NHCH$_2$CO$_2$H, $R_4$=H, $R_5$=(S,R)Me, $R_6$=H
Ip2: $R_1$=H, $R_2$=H, $R_3$=NHCH$_2$CO$_2$H, $R_4$=H, $R_5$=(S)Me, $R_6$=H
Iq2: $R_1$=H, $R_2$=H, $R_3$=NHCH$_2$CO$_2$H, $R_4$=H, $R_5$=(R)Me, $R_6$=H
Ia3: $R_1=\alpha$-OH, $R_2$=H, $R_3$=OH, $R_4=\alpha$-Me, $R_5$=(S,R)Me, $R_6$=H
Ib3: $R_1=\alpha$-OH, $R_2$=H, $R_3$=OH, $R_4=\alpha$-Me, $R_5$=(S)Me, $R_6$=H
Ic3: $R_1=\alpha$-OH, $R_2$=H, $R_3$=OH, $R_4=\alpha$-Me, $R_5$=(R)Me, $R_6$=H
Id3: $R_1=\beta$-OH, $R_2$=H, $R_3$=OH, $R_4=\alpha$-Me, $R_5$=(S,R)Me, $R_6$=H
Ie3: $R_1=\beta$-OH, $R_2$=H, $R_3$=OH, $R_4=\alpha$-Me, $R_5$=(S)Me, $R_6$=H
If3: $R_1=\beta$-OH, $R_2$=H, $R_3$=OH, $R_4=\alpha$-Me, $R_5$=(R)Me, $R_6$=H
Ig3: $R_1=\alpha$-OH, $R_2=\alpha$-OH, $R_3$=OH, $R_4=\alpha$-Me, $R_5$=(S,R)Me, $R_6$=H
Ih3: $R_1=\alpha$-OH, $R_2=\alpha$-OH, $R_3$=OH, $R_4=\alpha$-Me, $R_5$=(S)Me, $R_6$=H
Ii3: $R_1=\alpha$-OH, $R_2=\alpha$-OH, $R_3$=OH, $R_4=\alpha$-Me, $R_5$=(R)Me, $R_6$=H
Il3: $R_1=\beta$-OH, $R_2=\alpha$-OH, $R_3$=OH, $R_4=\alpha$-Me, $R_5$=(S,R)Me, $R_6$=H
Im3: $R_1=\beta$-OH, $R_2=\alpha$-OH, $R_3$=OH, $R_4=\alpha$-Me, $R_5$=(S)Me, $R_6$=H
In3: $R_1=\beta$-OH, $R_2=\alpha$-OH, $R_3$=OH, $R_4=\alpha$-Me, $R_5$=(R)Me, $R_6$=H
Ia4: $R_1=\alpha$-OH, $R_2$=H, $R_3$=NHCH$_2$CH$_2$SO$_3$H, $R_4=\alpha$-Me, $R_5$=(S,R)Me, $R_6$=H
Ib4: $R_1=\alpha$-OH, $R_2$=H, $R_3$=NHCH$_2$CH$_2$SO$_3$H, $R_4=\alpha$-Me, $R_5$=(S)Me, $R_6$=H
Ic4: $R_1=\alpha$-OH, $R_2$=H, $R_3$=NHCH$_2$CH$_2$SO$_3$H, $R_4=\alpha$-Me, $R_5$=(R)Me, $R_6$=H
Id4: $R_1=\beta$-OH, $R_2$=H, $R_3$=NHCH$_2$CH$_2$SO$_3$H, $R_4=\alpha$-Me, $R_5$=(S,R)Me, $R_6$=H
Ie4: $R_1=\beta$-OH, $R_2$=H, $R_3$=NHCH$_2$CH$_2$SO$_3$H, $R_4=\alpha$-Me, $R_5$=(S)Me, $R_6$=H
If4: $R_1=\beta$-OH, $R_2$=H, $R_3$=NHCH$_2$CH$_2$SO$_3$H, $R_4=\alpha$-Me, $R_5$=(R)Me, $R_6$=H
Ig4: $R_1=\alpha$-OH, $R_2=\alpha$-OH, $R_3$=NHCH$_2$CH$_2$SO$_3$H, $R_4=\alpha$-Me, $R_5$=(S,R)Me, $R_6$=H
Ih4: $R_1=\alpha$-OH, $R_2=\alpha$-OH, $R_3$=NHCH$_2$CH$_2$SO$_3$H, $R_4=\alpha$-Me, $R_5$=(S)Me, $R_6$=H
Ii4: $R_1=\alpha$-OH, $R_2=\alpha$-OH, $R_3$=NHCH$_2$CH$_2$SO$_3$H, $R_4=\alpha$-Me, $R_5$=(R)Me, $R_6$=H
Il4: $R_1=\beta$-OH, $R_2=\alpha$-OH, $R_3$=NHCH$_2$CH$_2$SO$_3$H, $R_4=\alpha$-Me, $R_5$=(S,R)Me, $R_6$=H
Im4: $R_1=\beta$-OH, $R_2=\alpha$-OH, $R_3$=NHCH$_2$CH$_2$SO$_3$H, $R_4=\alpha$-Me, $R_5$=(S)Me, $R_6$=H
In4: $R_1=\beta$-OH, $R_2=\alpha$-OH, $R_3$=NHCH$_2$CH$_2$SO$_3$H, $R_4=\alpha$-Me, $R_5$=(R)Me, $R_6$=H
Ia5: $R_1=\alpha$-OH, $R_2$=H, $R_3$=NHCH$_2$CO$_2$H, $R_4=\alpha$-Me, $R_5$=(S,R)Me, $R_6$=H
Ib5: $R_1=\alpha$-OH, $R_2$=H, $R_3$=NHCH$_2$CO$_2$H, $R_4=\alpha$-Me, $R_5$=(S)Me, $R_6$=H Icy: $R_1=\alpha$-OH, $R_2$=H, $R_3$=NHCH$_2$CO$_2$H, $R_4=\alpha$-Me, $R_5$=(R)Me, $R_6$=H
Id5: $R_1=\beta$-OH, $R_2$=H, $R_3$=NHCH$_2$CO$_2$H, $R_4=\alpha$-Me, $R_5$=(S,R)Me, $R_6$=H
Ie5: $R_1=\beta$-OH, $R_2$=H, $R_3$=NHCH$_2$CO$_2$H, $R_4=\alpha$-Me, $R_5$=(S)Me, $R_6$=H
If5: $R_1=\beta$-OH, $R_2$=H, $R_3$=NHCH$_2$CO$_2$H, $R_4=\alpha$-Me, $R_5$=(R)Me, $R_6$=H
Ig5: $R_1=\alpha$-OH, $R_2=\alpha$-OH, $R_3$=NHCH$_2$CO$_2$H, $R_4=\alpha$-Me, $R_5$=(S,R)Me, $R_6$=H
Ih5: $R_1=\alpha$-OH, $R_2=\alpha$-OH, $R_3$=NHCH$_2$CO$_2$H, $R_4=\alpha$-Me, $R_5$=(S)Me, $R_6$=H
Ii5: $R_1=\alpha$-OH, $R_2=\alpha$-OH, $R_3$=NHCH$_2$CO$_2$H, $R_4=\alpha$-Me, $R_5$=(R)Me, $R_6$=H
Il5: $R_1=\beta$-OH, $R_2=\alpha$-OH, $R_3$=NHCH$_2$CO$_2$H, $R_4=\alpha$-Me, $R_5$=(S,R)Me, $R_6$=H
Im5: $R_1=\beta$-OH, $R_2=\alpha$-OH, $R_3$=NHCH$_2$CO$_2$H, $R_4=\alpha$-Me, $R_5$=(S)Me, $R_6$=H
In5: $R_1=\beta$-OH, $R_2=\alpha$-OH, $R_3$=NHCH$_2$CO$_2$H, $R_4=\alpha$-Me, $R_5$=(R)Me, $R_6$=H The following compounds In6-In11 pertain to at least formula IA:

Ia6: $R_1$=OH, $R_2$=H, $R_3$=OH, $R_4$=H, $R_5$=(S,R)Me, $R_6$=H, $R_7$=Me
Ib6: $R_1$=OH, $R_2$=H, $R_3$=OH, $R_4$=H, $R_5$=(S)Me, $R_6$=H, $R_7$=Me
Ic6: $R_1$=OH, $R_2$=H, $R_3$=OH, $R_4$=H, $R_5$=(R)Me, $R_6$=H, $R_7$=Me
Id6: $R_1$=Me, $R_2$=H, $R_3$=OH, $R_4$=H, $R_5$=(S,R)Me, $R_6$=H, $R_7$=OH
Ie6: $R_1$=Me, $R_2$=H, $R_3$=OH, $R_4$=H, $R_5$=(S)Me, $R_6$=H, $R_7$=OH
If6: $R_1$=Me, $R_2$=H, $R_3$=OH, $R_4$=H, $R_5$=(R)Me, $R_6$=H, $R_7$=OH
Ig6: $R_1$=OH, $R_2=\alpha$-OH, $R_3$=OH, $R_4$=H, $R_5$=(S,R)Me, $R_6$=H, $R_7$=Me
Ih6: $R_1$=OH, $R_2=\alpha$-OH, $R_3$=OH, $R_4$=H, $R_5$=(S)Me, $R_6$=H, $R_7$=Me
Ii6: $R_1$=OH, $R_2=\alpha$-OH, $R_3$=OH, $R_4$=H, $R_5$=(R)Me, $R_6$=H, $R_7$=Me
Il6: $R_1$=Me, $R_2=\alpha$-OH, $R_3$=OH, $R_4$=H, $R_5$=(S,R)Me, $R_6$=H, $R_7$=OH
Im6: $R_1$=Me, $R_2=\alpha$-OH, $R_3$=OH, $R_4$=H, $R_5$=(S)Me, $R_6$=H, $R_7$=OH
In6: $R_1$=Me, $R_2=\alpha$-OH, $R_3$=OH, $R_4$=H, $R_5$=(R)Me, $R_6$=H, $R_7$=OH
Io6: $R_1$=H, $R_2$=H, $R_3$=OH, $R_4$=H, $R_5$=(S,R)Me, $R_6$=H, $R_7$=Me
Ip6: $R_1$=H, $R_2$=H, $R_3$=OH, $R_4$=H, $R_5$=(S)Me, $R_6$=H, $R_7$=Me
Iq6: $R_1$=H, $R_2$=H, $R_3$=OH, $R_4$=H, $R_5$=(R)Me, $R_6$=H, $R_7$=Me
Ia7: $R_1$=OH, $R_2$=H, $R_3$=NHCH$_2$CH$_2$SO$_3$H, $R_4$=H, $R_5$=(S,R)Me, $R_6$=H, $R_7$=Me
Ib7: $R_1$=OH, $R_2$=H, $R_3$=NHCH$_2$CH$_2$SO$_3$H, $R_4$=H, $R_5$=(S)Me, $R_6$=H, $R_7$=Me
Ic7: $R_1$=OH, $R_2$=H, $R_3$=NHCH$_2$CH$_2$SO$_3$H, $R_4$=H, $R_5$=(R)Me, $R_6$=H, $R_7$=Me
Id7: $R_1$=Me, $R_2$=H, $R_3$=NHCH$_2$CH$_2$SO$_3$H, $R_4$=H, $R_5$=(S,R)Me, $R_6$=H, $R_7$=OH
Ie7: $R_1$=Me, $R_2$=H, $R_3$=NHCH$_2$CH$_2$SO$_3$H, $R_4$=H, $R_5$=(S)Me, $R_6$=H, $R_7$=OH If7: $R_1$=Me, $R_2$=H, $R_3$=NHCH$_2$CH$_2$SO$_3$H, $R_4$=H, $R_5$=(R)Me, $R_6$=H, $R_7$=OH
Ig7: $R_1$=OH, $R_2$=α-OH, $R_3$=NHCH$_2$CH$_2$SO$_3$H, $R_4$=H, $R_5$=(S,R)Me, $R_6$=H, $R_7$=Me
Ih7: $R_1$=OH, $R_2$=α-OH, $R_3$=NHCH$_2$CH$_2$SO$_3$H, $R_4$=H, $R_5$=(S)Me, $R_6$=H, $R_7$=Me
Ii7: $R_1$=OH, $R_2$=α-OH, $R_3$=NHCH$_2$CH$_2$SO$_3$H, $R_4$=H, $R_5$=(R)Me, $R_6$=H, $R_7$=Me
Il7: $R_1$=Me, $R_2$=α-OH, $R_3$=NHCH$_2$CH$_2$SO$_3$H, $R_4$=H, $R_5$=(S,R)Me, $R_6$=H, $R_7$=OH
Im7: $R_1$=Me, $R_2$=α-OH, $R_3$=NHCH$_2$CH$_2$SO$_3$H, $R_4$=H, $R_5$=(S)Me, $R_6$=H, $R_7$=OH
In7: $R_1$=Me, $R_2$=α-OH, $R_3$=NHCH$_2$CH$_2$SO$_3$H, $R_4$=H, $R_5$=(R)Me, $R_6$=H, $R_7$=OH
Io7: $R_1$=H, $R_2$=H, $R_3$=NHCH$_2$CH$_2$SO$_3$H, $R_4$=H, $R_5$=(S,R)Me, $R_6$=H, $R_7$=Me
Ip7: $R_1$=H, $R_2$=H, $R_3$=NHCH$_2$CH$_2$SO$_3$H, $R_4$=H, $R_5$=(S)Me, $R_6$=H, $R_7$=Me
Iq7: $R_1$=H, $R_2$=H, $R_3$=NHCH$_2$CH$_2$SO$_3$H, $R_4$=H, $R_5$=(R)Me, $R_6$=H, $R_7$=Me
Ia8: $R_1$=OH, $R_2$=H, $R_3$=NHCH$_2$CO$_2$H, $R_4$=H, $R_5$=(S,R)Me, $R_6$=H, $R_7$=Me
Ib8: $R_1$=OH, $R_2$=H, $R_3$=NHCH$_2$CO$_2$H, $R_4$=H, $R_5$=(S)Me, $R_6$=H, $R_7$=Me
Ic8: $R_1$=OH, $R_2$=H, $R_3$=NHCH$_2$CO$_2$H, $R_4$=H, $R_5$=(R)Me, $R_6$=H, $R_7$=Me
Id8: $R_1$=Me, $R_2$=H, $R_3$=NHCH$_2$CO$_2$H, $R_4$=H, $R_5$=(S,R)Me, $R_6$=H, $R_7$=OH
Ie8: $R_1$=Me, $R_2$=H, $R_3$=NHCH$_2$CO$_2$H, $R_4$=H, $R_5$=(S)Me, $R_6$=H, $R_7$=OH
If8: $R_1$=Me, $R_2$=H, $R_3$=NHCH$_2$CO$_2$H, $R_4$=H, $R_5$=(R)Me, $R_6$=H, $R_7$=OH
Ig8: $R_1$=OH, $R_2$=α-OH, $R_3$=NHCH$_2$CO$_2$H, $R_4$=H, $R_5$=(S,R)Me, $R_6$=H, $R_7$=Me
Ih8: $R_1$=OH, $R_2$=α-OH, $R_3$=NHCH$_2$CO$_2$H, $R_4$=H, $R_5$=(S)Me, $R_6$=H, $R_7$=Me
Ii8: $R_1$=OH, $R_2$=α-OH, $R_3$=NHCH$_2$CO$_2$H, $R_4$=H, $R_5$=(R)Me, $R_6$=H, $R_7$=Me
Il8: $R_1$=Me, $R_2$=α-OH, $R_3$=NHCH$_2$CO$_2$H, $R_4$=H, $R_5$=(S,R)Me, $R_6$=H, $R_7$=OH
Im8: $R_1$=Me, $R_2$=α-OH, $R_3$=NHCH$_2$CO$_2$H, $R_4$=H, $R_5$=(S)Me, $R_6$=H, $R_7$=OH
In8: $R_1$=Me, $R_2$=α-OH, $R_3$=NHCH$_2$CO$_2$H, $R_4$=H, $R_5$=(R)Me, $R_6$=H, $R_7$=OH
Io8: $R_1$=H, $R_2$=H, $R_3$=NHCH$_2$CO$_2$H, $R_4$=H, $R_5$=(S,R)Me, $R_6$=H, $R_7$=Me
Ip8: $R_1$=H, $R_2$=H, $R_3$=NHCH$_2$CO$_2$H, $R_4$=H, $R_5$=(S)Me, $R_6$=H, $R_7$=Me
Iq8: $R_1$=H, $R_2$=H, $R_3$=NHCH$_2$CO$_2$H, $R_4$=H, $R_5$=(R)Me, $R_6$=H, $R_7$=Me
Ia9: $R_1$=OH, $R_2$=H, $R_3$=OH, $R_4$=α-Me, $R_5$=(S,R)Me, $R_6$=H, $R_7$=Me
Ib9: $R_1$=OH, $R_2$=H, $R_3$=OH, $R_4$=α-Me, $R_5$=(S)Me, $R_6$=H, $R_7$=Me
Ic9: $R_1$=OH, $R_2$=H, $R_3$=OH, $R_4$=α-Me, $R_5$=(R)Me, $R_6$=H, $R_7$=Me
Id9: $R_1$=Me, $R_2$=H, $R_3$=OH, $R_4$=α-Me, $R_5$=(S,R)Me, $R_6$=H, $R_7$=OH
Ie9: $R_1$=Me, $R_2$=H, $R_3$=OH, $R_4$=α-Me, $R_5$=(S)Me, $R_6$=H, $R_7$=OH
If9: $R_1$=Me, $R_2$=H, $R_3$=OH, $R_4$=α-Me, $R_5$=(R)Me, $R_6$=H, $R_7$=OH
Ig9: $R_1$=OH, $R_2$=α-OH, $R_3$=OH, $R_4$=α-Me, $R_5$=(S,R)Me, $R_6$=H, $R_7$=Me
Ih9: $R_1$=OH, $R_2$=α-OH, $R_3$=OH, $R_4$=α-Me, $R_5$=(S)Me, $R_6$=H, $R_7$=Me
Ii9: $R_1$=OH, $R_2$=α-OH, $R_3$=OH, $R_4$=α-Me, $R_5$=(R)Me, $R_6$=H, $R_7$=Me
Il9: $R_1$=Me, $R_2$=α-OH, $R_3$=OH, $R_4$=α-Me, $R_5$=(S,R)Me, $R_6$=H, $R_7$=OH
Im9: $R_1$=Me, $R_2$=α-OH, $R_3$=OH, $R_4$=α-Me, $R_5$=(S)Me, $R_6$=H, $R_7$=OH
In9: $R_1$=Me, $R_2$=α-OH, $R_3$=OH, $R_4$=α-Me, $R_5$=(R)Me, $R_6$=H, $R_7$=OH
Ia10: $R_1$=OH, $R_2$=H, $R_3$=NHCH$_2$CH$_2$SO$_3$H, $R_4$=α-Me, $R_5$=(S,R)Me, $R_6$=H, $R_7$=Me
Ib10: $R_1$=OH, $R_2$=H, $R_3$=NHCH$_2$CH$_2$SO$_3$H, $R_4$=α-Me, $R_5$=(S)Me, $R_6$=H, $R_7$=Me
Ic10: $R_1$=OH, $R_2$=H, $R_3$=NHCH$_2$CH$_2$SO$_3$H, $R_4$=α-Me, $R_5$=(R)Me, $R_6$=H, $R_7$=Me
Id10: $R_1$=Me, $R_2$=H, $R_3$=NHCH$_2$CH$_2$SO$_3$H, $R_4$=α-Me, $R_5$=(S,R)Me, $R_6$=H, $R_7$=OH
Ie10: $R_1$=Me, $R_2$=H, $R_3$=NHCH$_2$CH$_2$SO$_3$H, $R_4$=α-Me, $R_5$=(S)Me, $R_6$=H, $R_7$=OH
If10: $R_1$=Me, $R_2$=H, $R_3$=NHCH$_2$CH$_2$SO$_3$H, $R_4$=α-Me, $R_5$=(R)Me, $R_6$=H, $R_7$=OH
Ig10: $R_1$=OH, $R_2$=α-OH, $R_3$=NHCH$_2$CH$_2$SO$_3$H, $R_4$=α-Me, $R_5$=(S,R)Me, $R_6$=H, $R_7$=Me
Ih10: $R_1$=OH, $R_2$=α-OH, $R_3$=NHCH$_2$CH$_2$SO$_3$H, $R_4$=α-Me, $R_5$=(S)Me, $R_6$=H, $R_7$=Me
Ii10: $R_1$=OH, $R_2$=α-OH, $R_3$=NHCH$_2$CH$_2$SO$_3$H, $R_4$=α-Me, $R_5$=(R)Me, $R_6$=H, $R_7$=Me
Il10: $R_1$=Me, $R_2$=α-OH, $R_3$=NHCH$_2$CH$_2$SO$_3$H, $R_4$=α-Me, $R_5$=(S,R)Me, $R_6$=H, $R_7$=OH
Im10: $R_1$=Me, $R_2$=α-OH, $R_3$=NHCH$_2$CH$_2$SO$_3$H, $R_4$=α-Me, $R_5$=(S)Me, $R_6$=H, $R_7$=OH
In10: $R_1$=Me, $R_2$=α-OH, $R_3$=NHCH$_2$CH$_2$SO$_3$H, $R_4$=α-Me, $R_5$=(R)Me, $R_6$=H, $R_7$=OH
Ia11: $R_1$=OH, $R_2$=H, $R_3$=NHCH$_2$CO$_2$H, $R_4$=α-Me, $R_5$=(S,R)Me, $R_6$=H, $R_7$=Me
Ib11: $R_1$=OH, $R_2$=H, $R_3$=NHCH$_2$CO$_2$H, $R_4$=α-Me, $R_5$=(S)Me, $R_6$=H, $R_7$=Me
Ic11: $R_1$=OH, $R_2$=H, $R_3$=NHCH$_2$CO$_2$H, $R_4$=α-Me, $R_5$=(R)Me, $R_6$=H, $R_7$=Me
Id11: $R_1$=Me, $R_2$=H, $R_3$=NHCH$_2$CO$_2$H, $R_4$=α-Me, $R_5$=(S,R)Me, $R_6$=H, $R_7$=OH
Ie11: $R_1$=Me, $R_2$=H, $R_3$=NHCH$_2$CO$_2$H, $R_4$=α-Me, $R_5$=(S)Me, $R_6$=H, $R_7$=OH
If11: $R_1$=Me, $R_2$=H, $R_3$=NHCH$_2$CO$_2$H, $R_4$=α-Me, $R_5$=(R)Me, $R_6$=H, $R_7$=OH
Ig11: $R_1$=OH, $R_2$=α-OH, $R_3$=NHCH$_2$CO$_2$H, $R_4$=α-Me, $R_5$=(S,R)Me, $R_6$=H, $R_7$=Me
Ih11: $R_1$=OH, $R_2$=α-OH, $R_3$=NHCH$_2$CO$_2$H, $R_4$=α-Me, $R_5$=(S)Me, $R_6$=H, $R_7$=Me
Ii11: $R_1$=OH, $R_2$=α-OH, $R_3$=NHCH$_2$CO$_2$H, $R_4$=α-Me, $R_5$=(R)Me, $R_6$=H, $R_7$=Me
Il11: $R_1$=Me, $R_2$=α-OH, $R_3$=NHCH$_2$CO$_2$H, $R_4$=α-Me, $R_5$=(S,R)Me, $R_6$=H, $R_7$=OH
Im11: $R_1$=Me, $R_2$=α-OH, $R_3$=NHCH$_2$CO$_2$H, $R_4$=α-Me, $R_5$=(S)Me, $R_6$=H, $R_7$=OH
In11: $R_1$=Me, $R_2$=α-OH, $R_3$=NHCH$_2$CO$_2$H, $R_4$=α-Me, $R_5$=(R)Me, $R_6$=H, $R_7$=OH The following compounds Ia12-In17 pertain to at least formula II:

Ia12: $R_1$=OH, $R_2$=H, $R_4$=H, $R_5$=(S,R)Me, $R_6$=H, $R_7$=Me, $R_8$=H
Ib12: $R_1$=OH, $R_2$=H, $R_4$=H, $R_5$=(S)Me, $R_6$=H, $R_7$=Me, $R_8$=H
Ic12: $R_1$=OH, $R_2$=H, $R_4$=H, $R_5$=(R)Me, $R_6$=H, $R_7$=Me, $R_8$=H
Id12: $R_1$=Me, $R_2$=H, $R_4$=H, $R_5$=(S,R)Me, $R_6$=H, $R_7$=OH, $R_8$=H

Ie12: $R_1$=Me, $R_2$=H, $R_4$=H, $R_5$=(S)Me, $R_6$=H, $R_7$=OH, $R_8$=H
If12: $R_1$=Me, $R_2$=H, $R_4$=H, $R_5$=(R)Me, $R_6$=H, $R_7$=OH, $R_8$=H
Ig12: $R_1$=OH, $R_2$=α-OH, $R_4$=H, $R_5$=(S,R)Me, $R_6$=H, $R_7$=Me, $R_8$=H
Ih12: $R_1$=OH, $R_2$=α-OH, $R_4$=H, $R_5$=(S)Me, $R_6$=H, $R_7$=Me, $R_8$=H
Ii12: $R_1$=OH, $R_2$=α-OH, $R_4$=H, $R_5$=(R)Me, $R_6$=H, $R_7$=Me, $R_8$=H
Il12: $R_1$=Me, $R_2$=α-OH, $R_4$=H, $R_5$=(S,R)Me, $R_6$=H, $R_7$=OH, $R_8$=H
Im12: $R_1$=Me, $R_2$=α-OH, $R_4$=H, $R_5$=(S)Me, $R_6$=H, $R_7$=OH, $R_8$=H
In12: $R_1$=Me, $R_2$=α-OH, $R_4$=H, $R_5$=(R)Me, $R_6$=H, $R_7$=OH, $R_8$=H
Io12: $R_1$=H, $R_2$=H, $R_4$=H, $R_5$=(S,R)Me, $R_6$=H, $R_7$=Me, $R_8$=H
Ip12: $R_1$=H, $R_2$=H, $R_4$=H, $R_5$=(S)Me, $R_6$=H, $R_7$=Me, $R_8$=H
Iq12: $R_1$=H, $R_2$=H, $R_4$=H, $R_5$=(R)Me, $R_6$=H, $R_7$=Me, $R_8$=H
Ia13: $R_1$=OH, $R_2$=H, $R_4$=H, $R_5$=(S,R)Me, $R_6$=H, $R_7$=Me, $R_8$=H
Ib13: $R_1$=OH, $R_2$=H, $R_4$=H, $R_5$=(S)Me, $R_6$=H, $R_7$=Me, $R_8$=H
Ic13: $R_1$=OH, $R_2$=H, $R_4$=H, $R_5$=(R)Me, $R_6$=H, $R_7$=Me, $R_8$=H
Id13: $R_1$=Me, $R_2$=H, $R_4$=H, $R_5$=(S,R)Me, $R_6$=H, $R_7$=OH, $R_8$=H
Ie13: $R_1$=Me, $R_2$=H, $R_4$=H, $R_5$=(S)Me, $R_6$=H, $R_7$=OH, $R_8$=H
If13: $R_1$=Me, $R_2$=H, $R_4$=H, $R_5$=(R)Me, $R_6$=H, $R_7$=OH, $R_8$=H
Ig13: $R_1$=OH, $R_2$=α-OH, $R_4$=H, $R_5$=(S,R)Me, $R_6$=H, $R_7$=Me, $R_8$=H
Ih13: $R_1$=OH, $R_2$=α-OH, $R_4$=H, $R_5$=(S)Me, $R_6$=H, $R_7$=Me, $R_8$=H
Ii13: $R_1$=OH, $R_2$=α-OH, $R_4$=H, $R_5$=(R)Me, $R_6$=H, $R_7$=Me, $R_8$=H
Il13: $R_1$=Me, $R_2$=α-OH, $R_4$=H, $R_5$=(S,R)Me, $R_6$=H, $R_7$=OH, $R_8$=H
Im13: $R_1$=Me, $R_2$=α-OH, $R_4$=H, $R_5$=(S)Me, $R_6$=H, $R_7$=OH, $R_8$=H
In13: $R_1$=Me, $R_2$=α-OH, $R_4$=H, $R_5$=(R)Me, $R_6$=H, $R_7$=OH, $R_8$=H
Io13: $R_1$=H, $R_2$=H, $R_4$=H, $R_5$=(S,R)Me, $R_6$=H, $R_7$=Me, $R_8$=H
Ip13: $R_1$=H, $R_2$=H, $R_4$=H, $R_5$=(S)Me, $R_6$=H, $R_7$=Me, $R_8$=H
Iq13: $R_1$=H, $R_2$=H, $R_4$=H, $R_5$=(R)Me, $R_6$=H, $R_7$=Me, $R_8$=H
Ia14: $R_1$=OH, $R_2$=H, $R_4$=H, $R_5$=(S,R)Me, $R_6$=H, $R_7$=Me, $R_8$=H
Ib14: $R_1$=OH, $R_2$=H, $R_4$=H, $R_5$=(S)Me, $R_6$=H, $R_7$=Me, $R_8$=H
Ic14: $R_1$=OH, $R_2$=H, $R_4$=H, $R_5$=(R)Me, $R_6$=H, $R_7$=Me, $R_8$=H
Id14: $R_1$=Me, $R_2$=H, $R_4$=H, $R_5$=(S,R)Me, $R_6$=H, $R_7$=OH, $R_8$=H
Ie14: $R_1$=Me, $R_2$=H, $R_4$=H, $R_5$=(S)Me, $R_6$=H, $R_7$=OH, $R_8$=H
If14: $R_1$=Me, $R_2$=H, $R_4$=H, $R_5$=(R)Me, $R_6$=H, $R_7$=OH, $R_8$=H
Ig14: $R_1$=OH, $R_2$=α-OH, $R_4$=H, $R_5$=(S,R)Me, $R_6$=H, $R_7$=Me, $R_8$=H
Ih14: $R_1$=OH, $R_2$=α-OH, $R_4$=H, $R_5$=(S)Me, $R_6$=H, $R_7$=Me, $R_8$=H
Ii14: $R_1$=OH, $R_2$=α-OH, $R_4$=H, $R_5$=(R)Me, $R_6$=H, $R_7$=Me, $R_8$=H
Il14: $R_1$=Me, $R_2$=α-OH, $R_4$=H, $R_5$=(S,R)Me, $R_6$=H, $R_7$=OH, $R_8$=H
Im14: $R_1$=Me, $R_2$=α-OH, $R_4$=H, $R_5$=(S)Me, $R_6$=H, $R_7$=OH, $R_8$=H
In14: $R_1$=Me, $R_2$=α-OH, $R_4$=H, $R_5$=(R)Me, $R_6$=H, $R_7$=OH, $R_8$=H
Io14: $R_1$=H, $R_2$=H, $R_4$=H, $R_5$=(S,R)Me, $R_6$=H, $R_7$=Me, $R_8$=H
Ip14: $R_1$=H, $R_2$=H, $R_4$=H, $R_5$=(S)Me, $R_6$=H, $R_7$=Me, $R_8$=H
Iq14: $R_1$=H, $R_2$=H, $R_4$=H, $R_5$=(R)Me, $R_6$=H, $R_7$=Me, $R_8$=H
Ia15: $R_1$=OH, $R_2$=H, $R_4$=α-Me, $R_5$=(S,R)Me, $R_6$=H, $R_7$=Me, $R_8$=H
Ib15: $R_1$=OH, $R_2$=H, $R_4$=α-Me, $R_5$=(S)Me, $R_6$=H, $R_7$=Me, $R_8$=H
Ic15: $R_1$=OH, $R_2$=H, $R_4$=α-Me, $R_5$=(R)Me, $R_6$=H, $R_7$=Me, $R_8$=H
Id15: $R_1$=Me, $R_2$=H, $R_4$=α-Me, $R_5$=(S,R)Me, $R_6$=H, $R_7$=OH, $R_8$=H
Ie15: $R_1$=Me, $R_2$=H, $R_4$=α-Me, $R_5$=(S)Me, $R_6$=H, $R_7$=OH, $R_8$=H
If15: $R_1$=Me, $R_2$=H, $R_4$=α-Me, $R_5$=(R)Me, $R_6$=H, $R_7$=OH, $R_8$=H
Ig15: $R_1$=OH, $R_2$=α-OH, $R_4$=α-Me, $R_5$=(S,R)Me, $R_6$=H, $R_7$=Me, $R_8$=H
Ih15: $R_1$=OH, $R_2$=α-OH, $R_4$=α-Me, $R_5$=(S)Me, $R_6$=H, $R_7$=Me, $R_8$=H
Ii15: $R_1$=OH, $R_2$=α-OH, $R_4$=α-Me, $R_5$=(R)Me, $R_6$=H, $R_7$=Me, $R_8$=H
Il15: $R_1$=Me, $R_2$=α-OH, $R_4$=α-Me, $R_5$=(S,R)Me, $R_6$=H, $R_7$=OH, $R_8$=H
Im15: $R_1$=Me, $R_2$=α-OH, $R_4$=α-Me, $R_5$=(S)Me, $R_6$=H, $R_7$=OH, $R_8$=H
In15: $R_1$=Me, $R_2$=α-OH, $R_4$=α-Me, $R_5$=(R)Me, $R_6$=H, $R_7$=OH, $R_8$=H
Ia16: $R_1$=OH, $R_2$=H, $R_4$=α-Me, $R_5$=(S,R)Me, $R_6$=H, $R_7$=Me, $R_8$=H
Ib16: $R_1$=OH, $R_2$=H, $R_4$=α-Me, $R_5$=(S)Me, $R_6$=H, $R_7$=Me, $R_8$=H
Ic16: $R_1$=OH, $R_2$=H, $R_4$=α-Me, $R_5$=(R)Me, $R_6$=H, $R_7$=Me, $R_8$=H
Id16: $R_1$=Me, $R_2$=H, $R_4$=α-Me, $R_5$=(S,R)Me, $R_6$=H, $R_7$=OH, $R_8$=H
Ie16: $R_1$=Me, $R_2$=H, $R_4$=α-Me, $R_5$=(S)Me, $R_6$=H, $R_7$=OH, $R_8$=H
If16: $R_1$=Me, $R_2$=H, $R_4$=α-Me, $R_5$=(R)Me, $R_6$=H, $R_7$=OH, $R_8$=H
Ig16: $R_1$=OH, $R_2$=α-OH, $R_4$=α-Me, $R_5$=(S,R)Me, $R_6$=H, $R_7$=Me, $R_8$=H
Ih16: $R_1$=OH, $R_2$=α-OH, $R_4$=α-Me, $R_5$=(S)Me, $R_6$=H, $R_7$=Me, $R_8$=H
Ii16: $R_1$=OH, $R_2$=α-OH, $R_4$=α-Me, $R_5$=(R)Me, $R_6$=H, $R_7$=Me, $R_8$=H
Il16: $R_1$=Me, $R_2$=α-OH, $R_4$=α-Me, $R_5$=(S,R)Me, $R_6$=H, $R_7$=OH, $R_8$=H
Im16: $R_1$=Me, $R_2$=α-OH, $R_4$=α-Me, $R_5$=(S)Me, $R_6$=H, $R_7$=OH, $R_8$=H
In16: $R_1$=Me, $R_2$=α-OH, $R_4$=α-Me, $R_5$=(R)Me, $R_6$=H, $R_7$=OH, $R_8$=H
Ia17: $R_1$=OH, $R_2$=H, $R_4$=α-Me, $R_5$=(S,R)Me, $R_6$=H, $R_7$=Me, $R_8$=H
Ib17: $R_1$=OH, $R_2$=H, $R_4$=α-Me, $R_5$=(S)Me, $R_6$=H, $R_7$=Me, $R_8$=H
Ic17: $R_1$=OH, $R_2$=H, $R_4$=α-Me, $R_5$=(R)Me, $R_6$=H, $R_7$=Me, $R_8$=H
Id17: $R_1$=Me, $R_2$=H, $R_4$=α-Me, $R_5$=(S,R)Me, $R_6$=H, $R_7$=OH, $R_8$=H

Ie17: $R_1$=Me, $R_2$=H, $R_4$=α-Me, $R_5$=(S)Me, $R_6$=H, $R_7$=OH, $R_8$=H
If17: $R_1$=Me, $R_2$=H, $R_4$=α-Me, $R_5$=(R)Me, $R_6$=H, $R_7$=OH, $R_8$=H
Ig17: $R_1$=OH, $R_2$=α-OH, $R_4$=α-Me, $R_5$=(S,R)Me, $R_6$=H, $R_7$=Me, $R_8$=H
Ih17: $R_1$=OH, $R_2$=α-OH, $R_4$=α-Me, $R_5$=(S)Me, $R_6$=H, $R_7$=Me, $R_8$=H
Ii17: $R_1$=OH, $R_2$=α-OH, $R_4$=α-Me, $R_5$=(R)Me, $R_6$=H, $R_7$=Me, $R_8$=H
Il17: $R_1$=Me, $R_2$=α-OH, $R_4$=α-Me, $R_5$=(S,R)Me, $R_6$=H, $R_7$=OH, $R_8$=H
Im17: $R_1$=Me, $R_2$=α-OH, $R_4$=α-Me, $R_5$=(S)Me, $R_6$=H, $R_7$=OH, $R_8$=H
In17: $R_1$=Me, $R_2$=α-OH, $R_4$=α-Me, $R_5$=(R)Me, $R_6$=H, $R_7$=OH, $R_8$=H

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLE 1

Synthesis of TGR5 Modulators

The compounds of the invention, and related derivatives, can be synthesized by methods known to one skilled in the art. Detailed methods for synthesizing these compounds are described below. See, also, WO 02/072598, WO 2004/0007521, EP 1568706 and EP 135782. In the case of the compound where $R_1$ is hydrogen, $R_2$ and $R_3$ are hydroxy and $R_4$ is a lower alkyl group, the compound of formula (I) can be obtained in accordance with the following scheme:

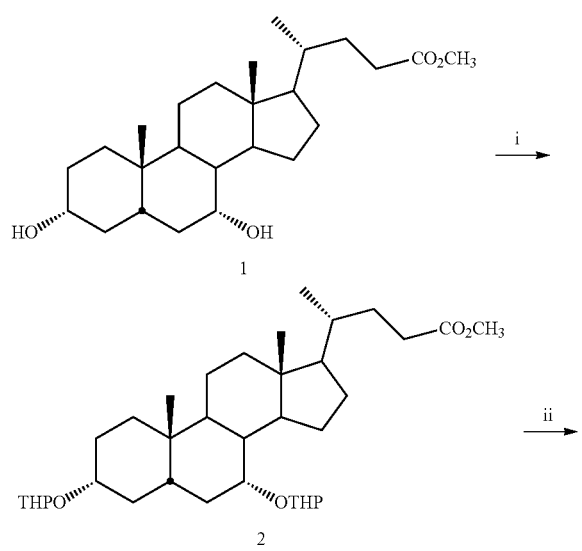

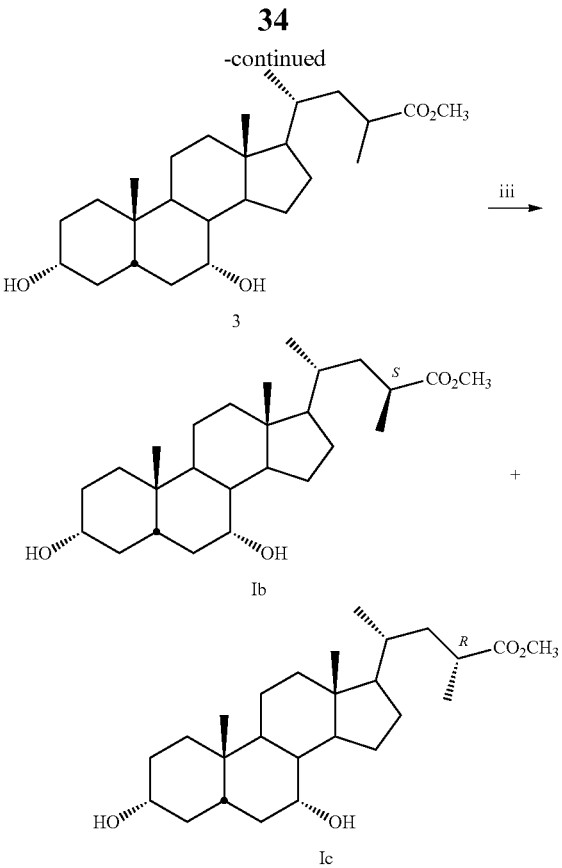

Scheme 1.
(i) 3,4-DHP, p-TSA, dioxane, r.t.; (ii) a) LDA, CH₃I, -78° C.; b) HCl, CH₃OH, r.t.; iii) NaOH, CH₃OH, reflux.

Methyl chenodeoxycholanoate (1) was protected in 3- and 7-position by treatment with 3,4-dihydro-2H-pyran in dioxane in presence of catalytic amount of p-toluenesulfonic acid (p-TSA) to give the corresponding 3α,7α-tetrahydropyranyloxy analog (2). Reaction of 2 with methyl iodide (or with an appropriate alkyl halide), at −78° C. using lithium diisopropylamide as a base and tetrahydrofuran (THF) as solvent, followed by treatment with methanolic HCl afforded the corresponding methyl 23-methyl-3α,7α-dihydroxy-5β-cholan-24-oate (3). Hydrolysis with alkali of the methyl ester 3 and purification by flash chromatography yielded the desired 23(S)-methyl-3α,7α-dihydroxy-5β-cholan-24-oic acid (Ib) and 23(R)-methyl-3α,7α-dihydroxy-5β-cholan-24-oic acid (Ic).

Preparation of 23(R)- and 23(S)-methyl-3α,7α-dihydroxy-5β-cholan-24-oic acid (Ib, Ic)

a) Methyl 3α,7α-ditetrahydropyranyloxy-5β-cholan-24-oate (2)

p-Toluenesulfonic acid (78 mg, 0.41 mmol), 3,4-dihydro-2H-pyrane (20.1 ml, 0.098 mol) were added to a solution of methyl 3α,7α-dihydroxy-5β-cholan-24-oate (1) (2.0 g, 4.9 mmol) in dioxane (6 mL). The reaction mixture was stirred at room temperature for 15 min. H₂O (50 mL) was then added and the mixture was partially concentrated under vacuum and extracted with EtOAc (3×50 mL). The combined organic fractions were washed with brine (1×50 mL), dried (Na₂SO₄) and evaporated under vacuum. The residue was purified by chromatography on silica gel column. Elution with light petroleum/ethyl acetate 80/20 afforded 2.5 g of the pure compound 2 (90% yield).

¹H-NMR (CDCl₃) δ: 0.64 (s, 3H, CH₃-18), 0.89 (s, 3H, CH₃-19), 0.92 (d, 3H, CH₃-21), 3.31-3.67 (m, 4H, —CH₂OCH—), 3.65 (s, 3H, CO₂CH₃), 3.67 (m, 1H, CH-3), 3.88 (brs, 1H, CH-7), 4.67 (brs, 1H, —O—CH—O—), 4.73 (brs, 1H, —O—CH—O—).

b) Methyl 23(R,S)-methyl-3α,7α-dihydroxy-5β-cholan-24-oate (3)

n-Butyl lithium (4.3 mL, 2.2 M solution in hexane) were added dropwise at −78° C. to a solution of diisopropylamine (1.4 mL, 10.1 mmol) in dry THF (50 mL). The system was kept to −78° C. for additional 30 min and then, methyl 3α,7α,12α-tetrahydropyranyloxy-5β-cholan-24-oate (2) (1.8 g, 3.2 mmol) dissolved in dry THF (14 mL) was added dropwise to the mixture. After 20 min methyl iodide (1.4 mL, 22.0 mmol) dissolved in dry THF (7 mL) was slowly added and the mixture was allowed to warm to room temperature overnight. The solvents were removed under vacuum and acidified by 10% HCl and extracted with EtOAc (5×50 mL), washed with 5% Na₂S₂O₃ solution (2×50 mL), dried (over anhydrous Na₂SO₄), filtered, and evaporated under vacuum. The crude residue was then treated with a solution of 2N HCl in MeOH (50 mL) for 12 h. The residue was evaporated under vacuum and taken up with EtOAc (100 mL), washed with a saturated NaHCO₃ solution (2×50 mL), dried (Na₂SO₄) and evaporated under vacuum. The residue was purified by silica gel flash chromatography. Elution with light petroleum/ethyl acetate 70/30 afforded 1.1 g (2.7 mmol) of the pure compound 3 (84% yield).

¹H-NMR (CDCl₃) δ: 0.62 (s, 3H, CH₃-18), 0.87 (s, 3H, CH₃-19), 0.92 (d, 3H, CH₃-21), 2.38 (m, 1H, CH-23), 3.27-3.40 (m, 1H, CH-3), 3.55 (brs, 1H, CH-7), 3.63 (s, 3H, CO₂CH₃).

c) 23(R)-Methyl-3α,7α-dihydroxy-5β-cholan-24-oic acid (Ib) and 23(S)-Methyl-3α,7α-dihydroxy-5β-cholan-24-oic acid (Ic)

Methyl 23-methyl-3α,7α-dihydroxy-5β-cholan-24-oate 0.97 g (2.3 mmol) was dissolved in MeOH (25 mL) and added with 10% NaOH in MeOH (5.7 mL, 14.2 mmol). The mixture was refluxed for 16 h. The mixture was acidified with 3N HCl and extracted with EtOAc (3×20 mL). The combined organic fractions were washed with brine (1×50 mL), dried (Na₂SO₄) and evaporated under vacuum. The residue was purified by silica gel flash chromatography. Elution with CHCl₃:MeOH (95/5) afforded 1.5 g (65%) of 23(S)-Methyl-3α,7α-dihydroxy-5β-cholan-24-oic acid and 330 mg of 23(R)-Methyl-3α,7α-dihydroxy-5β-cholan-24-oic acid.

23(S)-Methyl-3α,7α-dihydroxy-5β-cholan-24-oic acid (Ib): mp: 125-126° C. ¹H-NMR (CDCl₃+CD₃OD) δ: 0.44 (s, 3H, CH₃-18), 0.69 (s, 3H, CH₃-19), 0.73-0.76 (d, 3H, CH₃-21), 0.93-0.97 (d, 3H, —CH₃), 2.36 (m, 1H, CH-23), 3.15-3.38 (m, 1H, CH-3), 3.62 (brs, 1H, CH-7). ¹³C-NMR (CDCl₃+CD₃OD) δ: 11.55, 18.43, 18.87, 20.49, 22.69, 28.15, 28.57, 30.14, 32.65, 34.43, 34.61, 34.94, 35.23, 37.06, 39.17, 39.60, 40.81, 41.40, 42.57, 46.54, 50.29, 56.63, 68.24, 71.62, 179.99.

23(R)-Methyl-3α,7α-dihydroxy-5β-cholan-24-oic acid (Ic): mp: 163-164° C. ¹H-NMR (CDCl₃+CD₃OD) δ: 0.43 (s, 3H, CH₃-18), 0.65 (s, 3H, CH₃-19), 0.65-0.69 (d, 3H, CH₃-21), 0.83-0.86 (d, 3H, —CH₃), 2.20 (m, 1H, CH-23), 3.09-3.15 (m, 1H, CH-3), 3.58 (brs, 1H, CH-7). ¹³C-NMR (CDCl₃+CD₃OD) δ: 11.94, 16.40, 18.30, 20.93, 23.06, 23.89, 28.85, 30.52, 33.08, 34.16, 34.91, 35.38, 35.68, 37.14, 39.49, 39.64, 40.04, 40.17, 41.92, 43.05, 50.69, 57.10, 68.51, 72.01, 181.09.

EXAMPLE 2

Preparation of 23(S)- and 23(R)-methyl-6α-methyl-3α,7α-dihydroxy-5β-cholan-24-oic acid (Ib3, Ic3)

The following compounds were prepared by alkylation of 6α-methyl-3α,7α-dihydroxy-5β-cholan-24-oic acid according to the procedure of Example 1.

23(S)-Methyl-6α-methyl-3α,7α-dihydroxy-5β-cholan-24-oic acid (Ib3): mp: 98-100° C. ¹H-NMR (CDCl₃) δ: 0.63 (s, 3H, CH₃-18), 0.89 (s, 3H, CH₃-19), 0.92-1.00 (m, 6H, CH₃-21 and CH₃-6), 1.15-1.19 (d, 3H, —CH₃), 2.45-2.73 (m, 1H, CH-23), 3.31-3.52 (m, 1H, CH-3), 3.58 (brs, 1H, CH-7). ¹³C-NMR (CDCl₃) δ: 11.76, 15.72, 18.58, 18.88, 20.63, 23.11, 23.65, 28.19, 30.21, 30.47, 32.64, 33.79, 33.97, 34.61, 35.42, 35.66, 37.03, 39.60, 40.01, 40.71, 42.71, 47.35, 50.44, 56.60, 72.34, 72.87, 182.37.

23(R)-Methyl-3α,7α-dihydroxy-5β-cholan-24-oic acid (Ic3): mp: 89-90° C. ¹H-NMR (CDCl₃+CD₃OD) δ: 0.65 (s, 3H, CH₃-18), 0.88 (s, 3H, CH₃-19), 0.88-0.92 (m, 3H, CH₃-6), 0.95-0.99 (d, 3H, CH₃-21), 1.08-1.14 (d, 3H, —CH₃), 2.35 (m, 1H, CH-23), 3.29-3.48 (m, 1H, CH-3), 3.57 (brs, 1H, CH-7). ¹³C-NMR (CDCl₃+CD₃OD) δ: 11.70, 15.66, 16.02, 18.00, 20.61, 23.09, 23.60, 28.51, 30.39, 32.61, 33.72, 33.92, 35.38, 35.65, 36.33, 39.57, 39.94, 42.77, 47.30, 50.39, 56.53, 72.22, 72.83, 180.50.

EXAMPLE 3

Preparation of 23(R)- and 23(S)-methyl-3α,7α,12α-trihydroxy-5β-cholan-24-oic acid (Ih, Ii)

The following compounds were prepared by alkylation of 3α,7α,12α-trihydroxy-5β-cholan-24-oic acid according to the procedure of Example 1.

23(S)-Methyl-3α,7α,12α-trihydroxy-5β-cholan-24-oic acid (Ih): mp: 237-239° C. ¹H-NMR (CDCl₃) δ: 0.63 (s, 3H, CH₃-18), 0.87 (s, 3H, CH₃-19), 0.96-0.98 (m, 3H, CH₃-21), 1.07-1.11 (d, 3H, —CH₃), 2.44-2.73 (m, 1H, CH-23), 3.35-3.50 (m, 1H, CH-3), 3.82 (brs, 1H, CH-7), 3.95 (brs, 1H, CH-12). ¹³C-NMR (DMSO) δ: 12.72, 17.60, 19.24, 19.24, 23.00, 23.19, 26.59, 27.78, 28.88, 30.72, 34.77, 35.22, 35.66, 37.19, 41.84, 46.19, 47.27, 49.01, 66.69, 70.88, 71.45, 178.25.

23(R)-Methyl-3α,7α,12α-trihydroxy-5β-cholan-24-oic acid (Ii): mp: 221-223° C. ¹H-NMR (CDCl₃) δ: 0.63 (s, 3H, CH₃-18), 0.87 (s, 3H, CH₃-19), 0.96-0.98 (m, 3H, CH₃-21), 1.07-1.11 (d, 3H, —CH₃), 2.44-2.73 (m, 1H, CH-23), 3.35-3.50 (m, 1H, CH-3), 3.82 (brs, 1H, CH-7), 3.95 (brs, 1H, CH-12). ¹³C-NMR (DMSO) δ: 12.76, 16.88, 17.31, 23.04, 23.24, 26.62, 28.12, 28.94, 30.81, 33.97, 34.80, 35.28, 35.71, 37.20, 41.85, 46.29, 47.44, 66.67, 70.86, 71.45, 178.77.

EXAMPLE 4

Preparation of 23(R)- and 23(S)-methyl-6α-methyl-3α,7α,12α-trihydroxy-5β-cholan-24-oic acid (Ih3, Ii3)

The following compounds were prepared by alkylation of 6α-methyl-3α,7α,12α-trihydroxy-5β-cholan-24-oic acid according to the procedure of Example 1.

23 (S)-Methyl-6α-methyl-3α,7α,12α-trihydroxy-5β-cholan-24-oic acid (Ih3): mp: 131-134° C. ¹H-NMR (CDCl₃+CD₃OD) δ: 0.65 (s, 3H, CH₃-18), 0.87 (s, 3H, CH₃-19), 0.97-1.00 (m, 3H, CH₃-21), 1.14-1.18 (d, 3H, —CH₃), 1.23 (m, 1H, CH-6), 2.52 (m, 1H, CH-23), 3.32-3.50 (m, 1H, CH-3), 3.55 (brs, 1H, CH-7), 3.94 (brs, 1H, CH-12). ¹³C-NMR (CDCl₃+CD₃OD) δ: 12.43, 145.66, 17.62, 18.92, 22.70, 23.14, 26.21, 27.45, 28.01, 30.03, 33.44, 34.11, 34.42, 35.30, 36.71, 39.97, 40.45, 41.73, 46.45, 47.25, 72.13, 72.76, 73.01, 180.53.

23(R)-Methyl-6α-methyl-3α,7α,12α-trihydroxy-5β-cholan-24-oic acid (Ii3): mp: 109-110° C. ¹H-NMR (CD₃OD) δ: 0.72 (s, 3H, CH₃-18), 0.91 (s, 3H, CH₃-19), 1.07-1.11 (m, 6H, —CH₃ and CH₃-21), 2.37-2.53 (m, 1H, CH-23), 3.15-3.42 (m, 1H, CH-3), 3.53 (brs, 1H, CH-7) 3.97 (brs, 1H, CH-12). ¹³C-NMR (CD₃OD) δ: 11.61, 15.04, 15.32, 16.15, 22.04, 22.75, 26.27, 27.62, 28.18, 29.61, 32.91, 33.74, 34.31, 35.06, 35.18, 36.56, 39.70, 40.25, 41.68, 46.19, 46.31, 71.76, 71.77, 72.62, 180.11.

EXAMPLE 5

Preparation of 23(R)- and 23(S)-methyl-3α-hydroxy-5β-cholan-24-oic acid (Ip, Iq)

The following compounds were prepared by alkylation of 3α-hydroxy-5β-cholan-24-oic acid according to the procedure of Example 1.

23(S)-Methyl-3α-hydroxy-5β-cholan-24-oic acid (Ip): mp: 161-162° C. ¹H-NMR (CDCl₃+CD₃OD) δ: 0.60 (s, 3H, CH₃-18), 0.88 (s, 3H, CH₃-19), 0.92-1.01 (m, 3H, CH₃-21), 1.13-1.16 (d, 3H, —CH₃), 2.55 (m, 1H, CH-23), 3.60 (m, 1H, CH-3). ¹³C-NMR (CDCl₃+CD₃OD) δ: 11.97, 18.52, 18.87, 20.73, 23.30, 24.14, 26.34, 27.10, 28.15, 30.18, 34.48, 34.50, 35.23, 35.74, 36.06, 37.01, 40.13, 40.34, 40.74, 41.99, 42.68, 56.43, 56.75, 71.70, 181.42.

23(R)-Methyl-3α-hydroxy-5β-cholan-24-oic acid (Iq): mp: 152-153° C. ¹H-NMR (CDCl₃+CD₃OD) δ: 0.63 (s, 3H, CH₃-18), 0.89 (s, 3H, CH₃-19), 0.94-1.03 (m, 3H, CH₃-21), 2.45 (m, 1H, CH-23), 3.59 (m, 1H, CH-3). ¹³C-NMR (CD₃OD) δ: 11.98, 15.97, 18.00, 20.75, 23.31, 24.14, 26.34, 27.11, 28.48, 30.26, 33.68, 34.50, 35.26, 35.77, 36.15, 36.46, 39.59, 40.13, 40.36, 42.01, 42.79, 56.45, 56.76, 71.71, 181.02.

EXAMPLE 6

Biological Activity

The potency and efficacy of the compounds of the invention on TGR5 receptor was evaluated using in vitro assays. See, Kawamata, J. Biol. Chem. 2003, Vol. 278 No. 11, p. 9435-9440). Activity on FXR was assayed by fluorescence resonance energy transfer (FRET) for recruitment of the SRC-1 peptide to human FXR using a cell-free ELiSA. See, Blanchard et al. WO 00/37077.

TABLE 1

EC₅₀ (μM) of Example Compounds on FXR and TGR5 Receptor

| Compound | Structure | FXR Data | TGR5 Data |
|---|---|---|---|
| CDCA (ChenoDeoxyCholicAcid) | 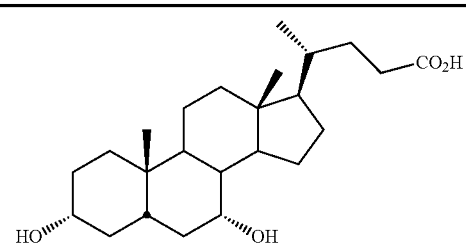 | EC₅₀: 8.6 μM Efficacy: 100% | EC₅₀: 4.0 μM Efficacy: 100% |
| 6α-MeCDCA | 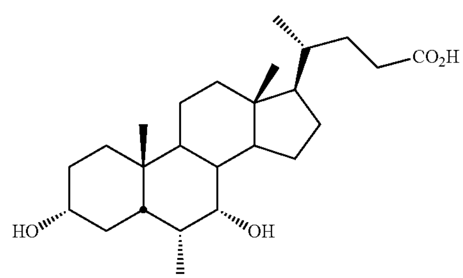 | EC₅₀: 0.21 μM Efficacy: 148% | EC₅₀: 0.37 μM Efficacy: 119% |
| 23(R + S)—Me—6MeCDCA (I3a) | 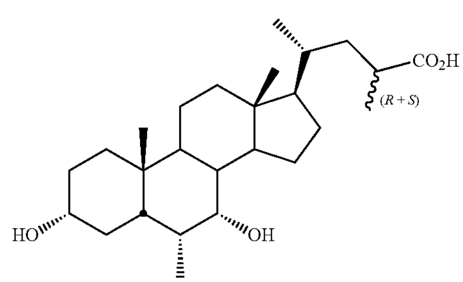 | EC₅₀: 15.62 μM Efficacy: 60% | EC₅₀: 0.11 μM Efficacy: 123% |

The compounds of the invention are potent and selective TGR5 modulators. The introduction of an alkyl group at the C-23 position of bile acid gives selectivity for the TGR5 receptor with respect to FXR. This is evident by the observation of the biological results obtained for CDCA, 6-MeCDCA and 6,23-diMe-CDCA (23-R,S isomers mixture) on FXR and TGR5 as shown in Table 1. 6,23-diMe-CDCA is 100-fold more potent on TGR5 with respect to the FXR receptor.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

What is claimed is:

1. A method of ameliorating a disease or condition selected from the group consisting of diabetes, insulin resistance, insulin hyposecretion, and pancreatic fatigue in a subject in need thereof, comprising administering to the subject a compound according to formula A:

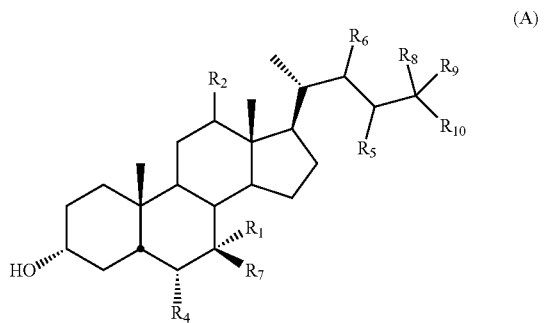

or a pharmaceutically acceptable salt thereof, wherein:
$R_1$ is hydrogen, hydroxy, substituted or unsubstituted alkyl, or halogen;
$R_2$ is hydrogen or α-hydroxy;
$R_3$ is hydrogen, hydroxy, $NH(CH_2)_m SO_3 H$, or $NH(CH_2)_n CO_2 H$;
$R_4$ is hydrogen, substituted or unsubstituted alkyl, or halogen;
$R_5$ is unsubstituted or substituted alkyl, or aryl;
$R_6$ is hydrogen, unsubstituted or substituted alkyl, or $R_5$ and $R_6$ taken together with the carbons to which they are attached form a ring of size 3, 4, 5, or 6 atoms;
$R_7$ is hydrogen, substituted or unsubstituted alkyl, or hydroxy;
$R_8$ is hydrogen or substituted or unsubstituted alkyl;
$R_9$ is hydrogen, substituted or unsubstituted alkyl, or $R_8$ and $R_9$ taken together form a carbonyl;
$R_{10}$ is $R_3$ or $SO_3 H$;
m is 0, 1, 2, 3, 4, or 5; and
n is 0, 1, 2, 3, 4, or 5.

2. The method of claim 1, wherein the disease or condition is diabetes.

3. The method of claim 1, wherein the disease or condition is insulin resistance.

4. The method of claim 1, wherein the disease or condition is insulin hyposecretion.

5. The method of claim 1, wherein the disease or condition is pancreatic fatigue.

6. The method of claim 1, wherein:
$R_1$ is hydroxy, substituted or unsubstituted alkyl, or halogen;
$R_2$ is α-hydroxy;
$R_4$ is substituted or unsubstituted alkyl, or halogen; and
$R_6$ is hydrogen, unsubstituted or substituted alkyl, or $R_5$ and $R_6$ taken together with the carbons to which they are attached form a ring of size 4, 5, or 6 atoms.

7. The method of claim 1, wherein:
$R_1$ is hydroxy or halogen;
$R_2$ is α-hydroxy;
$R_3$ is hydroxy, $NH(CH_2)_m SO_3 H$, or $NH(CH_2)_n CO_2 H$;
$R_4$ is substituted or unsubstituted alkyl, or halogen;
$R_6$ is hydrogen, or $R_5$ and $R_6$ taken together with the carbons to which they are attached form a ring of size 4, 5, or 6 atoms;
$R_7$ is hydrogen;
$R_8$ and $R_9$ form a carbonyl; and
$R_{10}$ is $R_3$.

8. The method of claim 1, wherein:
$R_1$ is hydroxy, substituted or unsubstituted alkyl, or halogen;
$R_2$ is α-hydroxy;
$R_3$ is hydroxy, $NH(CH_2)_m SO_3 H$, or $NH(CH_2)_n CO_2 H$;
$R_4$ is substituted or unsubstituted alkyl, or halogen;
$R_6$ is hydrogen, unsubstituted or substituted alkyl, or $R_5$ and $R_6$ taken together with the carbons to which they are attached form a ring of size 4, 5, or 6 atoms;
$R_8$ and $R_9$ form a carbonyl; and
$R_{10}$ is $R_3$.

9. The method of claim 1, wherein $R_9$ is hydrogen and $R_{10}$ is $SO_3 H$.

10. The method of claim 1, wherein $R_6$ is hydrogen.

11. The method of claim 10, wherein $R_2$ is α-hydroxy.

12. The method of claim 11, wherein $R_1$ hydroxy and $R_7$ is hydrogen.

13. The method of claim 12, wherein $R_8$ and $R_9$ taken together form a carbonyl and $R_{10}$ is $R_3$.

14. The method of claim 13, wherein $R_3$ is hydroxy.

15. The method of claim 14, wherein $R_5$ is unsubstituted alkyl.

16. The method of claim 15, wherein $R_5$ is in the S-configuration.

17. The method of claim 16, wherein $R_4$ is unsubstituted alkyl.

* * * * *